US006333374B1

(12) United States Patent
Chen

(10) Patent No.: US 6,333,374 B1
(45) Date of Patent: Dec. 25, 2001

(54) FLUFFY, STRONG, SOLID ELASTIC GELS, ARTICLES AND METHOD OF MAKING SAME

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 0 days.

(21) Appl. No.: 08/954,424

(22) Filed: Oct. 20, 1997

Related U.S. Application Data

(63) Continuation-in-part of application No. PCT/US97/17534, filed on Sep. 30, 1997, which is a continuation-in-part of application No. 08/581,125, filed on Dec. 29, 1995, now Pat. No. 5,962,572, which is a continuation-in-part of application No. 08/581,188, filed on Dec. 29, 1995, now abandoned, which is a continuation-in-part of application No. 08/909,487, filed on Aug. 12, 1997, now Pat. No. 6,050,871, which is a continuation-in-part of application No. 08/863,794, filed on May 27, 1997, which is a continuation-in-part of application No. 08/845,809, filed on Apr. 29, 1997, now Pat. No. 5,938,499, which is a continuation-in-part of application No. 08/581,191, filed on Dec. 29, 1995, now Pat. No. 5,760,117, which is a continuation-in-part of application No. 08/819,675, filed on Mar. 17, 1997, now Pat. No. 5,884,639, which is a continuation-in-part of application No. 08/719,817, filed on Sep. 30, 1996, which is a continuation-in-part of application No. 08/665,343, filed on Jun. 17, 1996, application No. 08/954,424, which is a continuation-in-part of application No. 08/612,586, filed on Mar. 8, 1996, which is a continuation-in-part of application No. PCT/US94/07314, filed on Jun. 27, 1994, which is a continuation-in-part of application No. PCT/US94/04278, filed on May 14, 1996, which is a continuation-in-part of application No. 08/288,690, filed on Aug. 11, 1994, now Pat. No. 5,633,286, which is a continuation-in-part of application No. 08/152,734, filed on Nov. 15, 1993, now Pat. No. 5,624,294, which is a continuation-in-part of application No. 08/114,688, filed on Aug. 30, 1993, now Pat. No. 5,475,890, which is a continuation-in-part of application No. 08/935,540, filed on Aug. 24, 1992, now Pat. No. 5,336,708, which is a continuation-in-part of application No. 07/876,118, filed on Apr. 29, 1992, now Pat. No. 5,324,222, which is a continuation-in-part of application No. 07/705,096, filed on May 23, 1991, now Pat. No. 5,655,947, which is a continuation-in-part of application No. 07/527,058, filed on May 21, 1990, now abandoned.

(51) Int. Cl.[7] ............................. C08L 23/00; C08L 53/00; C08K 3/20
(52) U.S. Cl. ...................... 524/270; 524/474; 524/476; 524/490; 524/505; 525/95; 525/98
(58) Field of Search .................................. 524/270, 474, 524/476, 490, 505; 525/95, 98

(56) References Cited

U.S. PATENT DOCUMENTS

| 3,660,849 | 5/1972 | Jonnes ........................................ 2/2.1 |
| 3,821,148 | 6/1974 | Makowski . |
| 3,821,149 | 6/1974 | Makowski ........................ 260/30.6 R |
| 3,827,999 | 8/1974 | Crossland ............................ 260/33.6 |
| 3,860,013 | 1/1975 | Czapor ................................... 132/91 |

(List continued on next page.)

FOREIGN PATENT DOCUMENTS

| 1268431 PCT/WO | 3/1972 | (GB) . |
| 88/00603 PCT/WO | 1/1988 | (WO) . |
| 90/05166 PCT/WO | 5/1990 | (WO) . |
| 91/05014 PCT/WO | 4/1991 | (WO) . |
| 93/05113 PCT/WO | 3/1993 | (WO) . |
| 93/23472 | 11/1993 | (WO) . |

OTHER PUBLICATIONS

"SiloLiner" Sales literature from Knit–Rite medical (Mar. 1, 1999 three pages).
ALPS South Corporation—Gel Liners: New! Easy Liner ELPX, ELDT and ELFR published fact sheet downloaded from the Internet on Aug. 10, 1999.
Chung P. Park and George P. Clingerman, "Compatibilization of Polyethylene–Polystyrene Blends with Ethylene–Syrene Random Copolymers", the Dow Chemical Company, May 1996.
Steve Hoenig, Bob Turley and Bill Van Volkenburgh, "Material Properties and Applications of Ethylene–Styrene Interpolymers", the Dow Chemical Company, Sep. 1996.
Y. Wilson Cheung and Martin J. Guest, "Structure, Thermal Transitions and Mechanical Properties of Ethylene/Styrene Copolymers", the Dow Chemical Company, May 1996. (17).
Teresa Plumley Karjaia, Y. Wilson Cheung and Martin J. Guest, "Melt Rheology and Processability of Ethylene/Styrene Interpolymers", the Dow Chemical Company, May 1997.
D. C. Prevorsek, et al., Origins of Damage Tolerance in Ultrastrong Polyethylene Fibers and Composites:, Journal of Polymer Science: Polymer Symposia No. 75, 81–104 (1993).
Chen, H., et al, "Classification of Ethylene–Styrene Interpolymers Based on Comonomer Content", J. Appl. Polym. Sci., 1998, 70, 109.
Alizadeh, et al., "Effect of Topological Constraints on The Crystallization Behavior of Ethylene/alpha–Olefin Copolymers", PMSE, vol. 81, pp. 248–249, Aug. 22–26, 1999.
Guest, et al., "Structure/Property Relationships of Semi–Crystalline Ethylene–Styrene Interpolymers (ESI)", PMSE, vol., 81, pp. 371–372, Aug. 22–26, 1999.

(List continued on next page.)

Primary Examiner—Herbert J. Lilling

(57) ABSTRACT

Novel fluffy, solid, strong elastic gels exhibiting resistance to elastic deformation, capable of shape-memory recovery, being dimensionally stable and having a density of at least less than about 0.60 g/cm³, a gel rigidity of from about 20 to about 3,000 gram Bloom, and an elongation of at least 200% can be formed with or physically interlocked with selected material substrates to form composites including any sequential additions or permutations of said combinations of gels and substrates.

13 Claims, No Drawings

U.S. PATENT DOCUMENTS

| | | | |
|---|---|---|---|
| 4,102,807 | * 7/1978 | Iwama et al. | 252/316 |
| 4,136,699 | 1/1979 | Collins | 128/290 |
| 4,151,057 | 4/1979 | St. Clair . | |
| 4,176,240 | 11/1979 | Sabia | 174/23 |
| 4,225,500 | * 9/1980 | Newton | 524/474 |
| 4,259,540 | 3/1981 | Sabia . | |
| 4,351,913 | 9/1982 | Patel . | |
| 4,361,508 | 11/1982 | Bourland | 523/173 |
| 4,369,284 | 1/1983 | Chen . | |
| 4,432,607 | 2/1984 | Levy | 350/96.34 |
| 4,492,428 | 1/1985 | Levy . | |
| 4,497,538 | 2/1985 | Patel . | |
| 4,509,821 | 4/1985 | Stenger | 350/96.23 |
| 4,600,261 | 7/1986 | Debbaut . | |
| 4,610,738 | 9/1986 | Jervis | 156/49 |
| 4,618,213 | 10/1986 | Chen . | |
| 4,643,924 | 2/1987 | Uken | 428/35 |
| 4,662,692 | 5/1987 | Uken | 339/96 |
| 4,678,664 | 7/1987 | Schmolka | 424/65 |
| 4,680,233 | 7/1987 | Camin | 428/424.6 |
| 4,690,831 | 9/1987 | Uken | 427/44 |
| 4,692,369 | 9/1987 | Nomi | 428/198 |
| 4,709,982 | 12/1987 | Corne | 427/44 |
| 4,716,183 | 12/1987 | Gamarra | 522/90 |
| 4,721,832 | 1/1988 | Toy | 174/87 |
| 4,764,535 | 8/1988 | Leicht . | |
| 4,798,853 | 1/1989 | Handlin | 523/173 |
| 4,801,346 | 1/1989 | Huddleston . | |
| 4,822,834 | 4/1989 | Blevins | 524/427 |
| 4,833,193 | 5/1989 | Sieverding . | |
| 4,842,931 | 6/1989 | Zook | 428/354 |
| 4,864,725 | 9/1989 | Debbaut | 29/871 |
| 4,865,905 | 9/1989 | Uken | 428/220 |
| 4,880,676 | 11/1989 | Pulgcerver | 428/35.7 |
| 4,880,878 | 11/1989 | Himes | 525/89 |
| 4,883,431 | 11/1989 | Uken . | |
| 4,888,070 | 12/1989 | Clark . | |
| 4,889,171 | 12/1989 | Covington | 428/304 |
| 4,889,403 | 12/1989 | Zucker . | |
| 4,900,877 | 2/1990 | Dubrow | 174/35 |
| 4,909,756 | 3/1990 | Jervis . | |
| 4,929,211 | 5/1990 | Resnick | 446/14 |
| 4,942,270 | 7/1990 | Gamarra | 174/93 |
| 4,944,363 | 7/1990 | Osher | 273/58 |
| 4,944,973 | 7/1990 | Follette . | |
| 4,968,747 | 11/1990 | Mallikarjun | 525/74 |
| 4,983,008 | 1/1991 | Campbell | 350/96.16 |
| 5,026,054 | 6/1991 | Osher | 273/58 |
| 5,059,748 | 10/1991 | Allen | 174/87 |
| 5,068,138 | 11/1991 | Mitchell | 428/36.8 |
| 5,085,597 | 2/1992 | Story | 439/521 |
| 5,088,734 | 2/1992 | Glava | 273/73 |
| 5,098,421 | 3/1992 | Zook | 604/367 |
| 5,126,182 | 6/1992 | Douglas | 428/90 |
| 5,149,736 | 9/1992 | Gamarra | 524/490 |
| 5,153,254 | 10/1992 | Chen | 524/505 |
| 5,159,022 | 10/1992 | Ikematu | 525/250 |
| 5,167,649 | 12/1992 | Zook | 604/307 |
| 5,173,573 | 12/1992 | Jervis | 174/138 |
| 5,177,143 | 1/1993 | Toy | 524/848 |
| 5,181,914 | 1/1993 | Zook | 604/307 |
| 5,191,752 | 3/1993 | Murphy | 54/44.5 |
| 5,221,534 | 6/1993 | Deslauriers | 424/78.03 |
| 5,239,723 | 8/1993 | Chen | 15/104 |
| 5,262,468 | 11/1993 | Chen | 524/476 |
| 5,313,019 | 5/1994 | Brusselmans | 174/93 |
| 5,324,222 | 6/1994 | Chen | 446/34 |
| 5,330,452 | 7/1994 | Zook | 604/307 |
| 5,334,646 | 8/1994 | Chen | 524/474 |
| 5,336,708 | 8/1994 | Chen | 524/474 |
| 5,459,193 | 10/1995 | Anderson | 524/505 |
| 5,475,890 | 12/1995 | Chen | 15/104 |
| 5,479,952 | 1/1996 | Zachariades | 132/321 |
| 5,559,165 | 9/1996 | Paul | 523/111 |
| 5,590,430 | * 1/1997 | Sereboff | 5/655.5 |
| 5,606,149 | 2/1997 | Yaworski | 174/92 |
| 5,618,882 | 4/1997 | Hammond | 525/92 D |
| 5,624,294 | 4/1997 | Chen | 446/253 |
| 5,626,657 | 5/1997 | Pearce | 106/122 |
| 5,633,286 | 5/1997 | Chen | 524/474 |
| 5,655,947 | 8/1997 | Chen | 446/46 |
| 5,863,977 | 1/1999 | Fisher . | |
| 5,872,201 | 2/1999 | Cheung . | |
| 5,884,639 | * 3/1999 | Chen | 524/270 |
| 5,929,138 | 7/1999 | Mercer . | |
| 5,952,396 | 9/1999 | Chang | 522/1 |
| 5,994,446 | 11/1999 | Graykys . | |
| 5,994,450 | 11/1999 | Pearce | 524/505 |

OTHER PUBLICATIONS

"Styrene–Diene Triblock Copolymers: Orientation Conditions and Mechanical Properties of the Oriented Materials" A. Weill and R. Pixa, Journal of Polymer Science Polymer Symposium 58, 381–394 (1977).

Tuftec Trade Literature, Asani Chemical Co., LTD., Synthetic Rubber Division, English and Japanese 14 pages.

Septon Trade Literature, Kuraray Co., LTD. 1995.8 (4,000) 15 pages.

Shell Chemical Co., Data Sheets: EKP–207 (093094–02) and L–1203 (SC:2384–950.

SC:1102–89 Shell Chemical Technical Bulletin"KRATON® Thermoplastic Rubber in Oil Gels", Apr. 1989.

"TUFTEC" —its characteristics and applications, Assahi Chemical. SEPTON, High Performance Thermoplstic Rubber, Kurraray Co., LTD., 1995.

Kraton Polymers, May 1997, Shell Chemical Company.

Melt Miscibility in Blends of Polypropylene, Polystryenhe–Block–Poly (Ethylene–Sat–Butylne)–Block–Polystyrene, and Processing Oil from Melting Point Depression, Ohlesson et al., Polymer Engineering and Science, 1996, vol. 36, No. 11.

Blends and Thermoplastic Interpenetrating Polymer Networks of Polypropytlene and Polystyrene–Block–Poly (Ethylene–Stat–Butylene)–Block–Polystyrene Triblock Copolymer. 1: Morphology and Structure–Related Properties, Ohlesson, et al., Polymer Engineering and Science, Feb. 1996, vol. 36, No. 4.

Migration and Blooming of Waxes to the Surface of Rubber Vulcanizates, Nah, et al., J. of Polymer Science: Polymer Physics Ed., vol. 18, 511–521 (1980).

* cited by examiner

«FLUFFY, STRONG, SOLID ELASTIC GELS, ARTICLES AND METHOD OF MAKING SAME»

RELATED APPLICATIONS AND PATENTS

This application is a continuation-in-part application of pending applications PCT/US97/17534, filed Sep. 30, 1997 now Ser. No. 09/230,940, filed Feb. 3, 1999; Ser. No. 08/581,125, filed Dec. 29, 1995 now U.S. Pat. No. 5,962,572; Ser. No. 08/581,188, filed Dec. 29, 1995 now abandoned; Ser. No. 08/909,487, filed Aug. 12, 1997 now U.S. Pat. No. 6,050,871; Ser. No. 08/581,191, filed Dec. 29, 1995 now U.S. Pat. No. 5,760,117; Ser. No. 08/845,809, filed Apr. 29, 1997 now U.S. Pat. No. 5,938,499; Ser. No. 08/863,794, filed May 27, 1997; Ser. No. 08/819,675, filed Mar. 17, 1997, now U.S. Pat. No. 5,884,639; Ser. No. 08/719,817, filed Sep. 30, 1996; Ser. No. 08/665,343, filed Jun. 17, 1996; Ser. No. 08/612,586, filed Mar. 8, 1996; PCT/US94/07314 filed Jun. 27, 1994 now Ser. No. 08/256,235 filed Jun. 27, 1994 now U.S. Pat. No. 5,868,597, PCT/US94/04278, filed Apr. 19, 1994 now Ser. No. 08/211,781 filed May 14, 1996 now U.S. Pat No. 6,033,283; Ser. No. 08/288/690, filed Aug. 11, 1994 now U.S. Pat. No. 5,633,286; Ser. No. 08/152,734, filed Nov. 15, 1993 now U.S. Pat. No. 5,624,294; Ser. No. 08/114,688, filed Aug. 30, 1993 now U.S. Pat. No. 5,475,890; Ser. No. 08/935,540, filed Aug. 24, 1992 now U.S. Pat. No. 5,336,708; Ser. No. 07/876,118, filed Apr. 29, 1992 now U.S. Pat. No. 5,324,222; Ser. No. 07/705,096, filed May 23, 1991 now U.S. Pat. No. 5,655,947, which are continuation-in-part applications of Ser. No. 07/527,058 filed May 21, 1990 now abandoned.

FIELD OF THE INVENTION

The present invention relates to novel gel compositions, articles, and method of making same.

BACKGROUND OF THE INVENTION

The closest known prior arts are: U.S. Pat. Nos. 3,683,104; 3,843,568; 4,351,913; 5,421,874; 5,422,378; 5,592,706; and 5,626,657. Both '104 and '568 are directed to mixtures of petrolatum, partially crosslinked polymers and hollow synthetic thermoplastic particles of styrene and acrylonitrile. U.S. Patent '378 is directed to styrene foam made by the use of a blowing agent. Patent '913 is directed to waterproofing cable filling materials of block copolymers dissolved in oils with a minimal amount of hollow microspheres. The other '874, '706, and '657 patents are directed to free moving, sliding microsphere-liquid and liquid polymer mixtures. In particular, U.S. Patent '657 is directed to conforming, movable, flowable, shape changing, shearable, ambient temperature microsphere-liquid mixtures. It teaches forming a SEBS visco-elastic oil fluid at between near 350° F. to 365° F. and held at 365° F. for about four hours with continued agitation. After the visco-elastic fluid has cooled to ambient temperature, acrylic PM 6545 microspheres are added to the fluid to make for example a composite mixture having a specific gravity of about 0.12. The resulting mixture has little or no memory, is readily flowable and shearable, does not have shape memory, and the fluid amount of the mixture is insufficient to disperse the microspheres in the lubricant. Microspheres suitable for use include expanded or unexpanded DE (091-80) phenolic microspheres from Expandcel, Inc. U.S. There is no suggestion in '657, no teaching, no reason that any unexpanded microspheres after mixing with lubricant is ever heated to a sufficient temperature necessary to expand the unexpanded microspheres. It appears that the unexpanded microsphere lubricant mixture is used as is without any heating to expand the microspheres. U.S. Pat. No. 5,590,430 is directed to gel filled deformable cushion and padding.

SUMMARY OF THE INVENTION

I have unexpectedly discovered novel compositions and articles comprising a heat formable, fluffy, light, soft, airy, solid, strong elastic gelatinous elastomer composition, $G_n$, exhibiting substantially complete resistance to elastic deformation, capable of substantial complete shape-memory recovery and being dimensionally stable, wherein when n is a subscript of G, n denotes the same or a different gel rigidity. The fluffy, elastic solid gelatinous elastomer composition, $G_n$, is formed from (I) 100 parts by weight of at least one or more high viscosity block copolymer; (II) about 300 to about 1,600 parts by weight of a plasticizing oil; (III) a selected amount of one or more heat expandable plastic or synthetic particulate material dispersed in an ordered, random, homogeneous, nonhomogeneous, stratified, partially stratified or one or more separated phases. The dispersed particulate material is capable of producing a predetermined volume of closed cell particulate dispersion forming said $G_n$ having a density of at least less than about 0.60 g/cm$^3$, a gel rigidity of from about 20 to about 3,000 gram Bloom, and an elongation of at least 200%. The $G_n$ can also be formed with or physically interlocked with a selected material $M_n$ to form a composite comprising combinations of $G_n$ and $M_n$, any sequential additions or permutations of said combinations $M_nG_n$, $G_nM_nG_n$, $M_nG_nM_n$, $M_nG_nG_n$, $M_nM_nG_n$, $M_nG_nG_nG_n$, $M_nM_nM_nG_n$, including $M_nG_nG_nM_n$, $G_nM_nG_nM_n$, $G_nG_nM_nG_n$, $M_nG_nM_nM_n$, $M_nG_nM_nG_n$, $G_nM_nG_nG_n$, $G_nM_nM_nG_n$, $G_nG_nM_nM_n$, $G_nG_nM_nG_nM_n$, $G_nM_nG_nM_nM_n$, $G_nM_nG_nM_nG_n$, $G_nM_nM_nG_nG_n$, $G_nG_nG_nM_nM_n$, $M_nG_nG_nM_nG_n$, $M_nG_nM_nG_nM_n$, $G_nG_nM_nM_nM_n$, $G_nM_nM_nG_nM_n$, $G_nG_nG_nM_nG_nG_n$, $M_nG_nM_nG_nM_nG_n$, $G_nG_nM_nM_nG_n$, $G_nG_nM_nG_nM_nG_n$, $G_nM_nG_nM_nG_nM_n$, $G_nM_nM_nG_nG_nM_n$, $M_nG_nG_nM_nM_n$, $M_nG_nG_nM_nG_nM_n$, $G_nG_nM_nG_nM_nG_n$, $M_nG_nM_nG_nM_nM_n$, $G_nG_nM_nG_nG_nM_n$, $G_nG_nM_nG_nG_nM_nM_n$, $G_nG_nM_nG_nG_nM_n$, $M_nG_nM_nG_nG_nM_n$, $G_nG_nM_nG_nM_nG_nG_n$, $M_nG_nM_nG_nG_nM_nM_n$, $M_nM_nG_nG_nM_nM_nM_n$, $M_nG_nM_nG_nG_nM_n$, $G_nM_nG_nM_nG_nM_nG_n$, $M_nG_nM_nG_nM_nM_nG_n$, $G_nM_nM_nG_nM_nM_nG_n$, $M_nG_nG_nM_nG_nG_nM_n$, $G_nM_nG_nM_nG_nM_nG_nM_n$, $G_nG_nM_nM_nG_nG_nM_nM_n$, $G_nG_nM_nG_nG_nM_nG_nG_n$, $M_nG_nG_nM_nG_nG_nM_n$, $G_nM_nG_nG_nM_nG_nG_nM_nG_n$, $G_nG_nM_nG_nM_nG_nM_nG_nG_n$, or $G_nM_nG_nM_nG_nM_nG_nM_nG_nM_nG_nM_nG_n$, wherein when n is a subscript of M, n is the same or different selected from the group consisting of foam, plastic, fabric, metal, concrete, wood, glass, ceramics, synthetic resin, synthetic fibers or refractory materials. The (I) block copolymer component(s) forming the $G_n$ of the invention is a linear, multi-arm, branched, or star shaped copolymer of the general configuration poly(styrene-ethylene-butylene-styrene), poly(styrene-ethylene-propylene-styrene), poly(styrene-ethylene-styrene), poly(styrene-butylene-styrene), poly(styrene-ethylene-ethylene/butylene-styrene), poly(styrene-ethylene-ethylene/propylene-styrene), poly(styrene-butylene-ethylene/propylene-styrene), poly(styrene-butylene-ethylene/butylene-styrene), poly(styrene-ethylene/propylene-ethylene-styrene), poly(styrene-ethylene-ethylene/butylene-butylene-styrene), poly(styrene-ethylene/propylene-butylene-styrene), poly(styrene-butylene-ethylene/butylene-butylene-styrene), poly(styrene-ethylene-butylene-ethylene/butylene-styrene), poly(styrene-ethylene-butylene-ethylene/propylene-styrene), poly(styrene-ethylene/butylene-ethylene/propylene-styrene), poly(styrene-ethylene-ethylene/butylene-ethylene/propylene-styrene), poly(styrene-ethylene-ethylene/propylene-ethylene/butylene-styrene), poly(styrene-butylene-ethylene/butylene-ethylene/propylene-styrene), poly(styrene-butylene-ethylene/propylene-ethylene/butylene-styrene), poly(styrene-ethylene-ethylene/propylene-ethylene-ethylene/propylene-styrene), poly(styrene-ethylene-ethylene/propylene-ethylene-ethylene/butylene-styrene), poly(styrene-ethylene/propylene-butylene-ethylene/propylene-styrene), poly(styrene-butylene-ethylene/butylene-butylene-ethylene/butylene-styrene), poly(styrene-butylene-ethylene/butylene-butylene-ethylene/propylene-styrene), poly(styrene-ethylene-ethylene/butylene-butylene-ethylene/propylene-styrene), poly(styrene-ethylene-ethylene/propylene-butylene-ethylene/butylene-styrene), poly(styrene-ethylene-ethylene/propylene-ethylene-ethylene/propylene-ethylene-styrene), poly(styrene-butylene-ethylene/propylene-butylene-ethylene/propylene-butylene-styrene), poly(styrene-ethylene-ethylene/propylene-ethylene-ethylene/butylene-styrene), poly(styrene-ethylene-ethylene/propylene-ethylene-ethylene/propylene-ethylene/butylene-styrene), poly(styrene-ethylene-ethylene/propylene-ethylene-ethylene/propylene-ethylene-styrene), poly(styrene-ethylene-ethylene/propylene-ethylene/butylene-ethylene/propylene-ethylene/butylene-butylene-styrene), poly(styrene-ethylene-butylene)$_n$, poly(styrene-ethylene-propylene)$_n$, poly(styrene-ethylene)$_n$, poly(styrene-butylene)$_n$, poly(styrene-ethylene-ethylene/butylene)$_n$, poly(styrene-ethylene-ethylene/propylene)$_n$, poly(styrene-butylene-ethylene/propylene)$_n$, poly(styrene-butylene-ethylene/butylene)$_n$, poly(styrene-ethylene-ethylene/propylene-ethylene)$_n$, poly(styrene-ethylene-ethylene/butylene-butylene)$_n$, poly(styrene-butylene-ethylene/propylene-butylene)$_n$, poly(styrene-butylene-ethylene/butylene-butylene)$_n$, poly(styrene-ethylene-butylene-ethylene/butylene)$_n$, poly(styrene-ethylene-butylene-ethylene/propylene)$_n$, poly(styrene-ethylene-butylene-ethylene/propylene)$_n$, poly(styrene-ethylene-ethylene/butylene-ethylene/propylene)$_n$, poly(styrene-ethylene-ethylene/propylene-ethylene/butylene)$_n$, poly(styrene-butylene-ethylene/butylene-ethylene/propylene)$_n$, poly(styrene-butylene-ethylene/propylene-ethylene/butylene)$_n$, poly(styrene-ethylene-ethylene/propylene-ethylene-ethylene/propylene)$_n$, poly(styrene-ethylene-ethylene/propylene-ethylene-ethylene/butylene)$_n$, poly(styrene-ethylene/propylene-butylene-ethylene/propylene)$_n$, poly(styrene-butylene-ethylene/butylene-butylene-ethylene/butylene)$_n$, poly(styrene-butylene-ethylene/butylene-butylene-ethylene/propylene)$_n$, poly(styrene-ethylene-ethylene/butylene-butylene-ethylene/propylene)$_n$, poly(styrene-ethylene-ethylene/propylene-butylene-ethylene/propylene)$_n$, poly(styrene-ethylene-ethylene/propylene-ethylene-ethylene/propylene)$_n$, poly(styrene-ethylene-butylene/propylene-butylene-ethylene/propylene-butylene)$_n$, poly(styrene-ethylene-ethylene/propylene-butylene-ethylene/propylene-butylene)$_n$, poly(styrene-ethylene-ethylene/propylene-ethylene-ethylene/butylene)$_n$, poly(styrene-ethylene-ethylene/propylene-ethylene-ethylene/propylene-ethylene/butylene)$_n$, poly(styrene-ethylene-ethylene/propylene-ethylene/propylene)$_n$, poly(styrene-ethylene-ethylene/propylene-ethylene/butylene-ethylene/propylene-ethylene/butylene-butylene)$_n$ or a mixture thereof. The $G_n$ can also be made with or without a (IV) selected amount of at least one polar polymer selected from the group consisting of ethylene-butyl acrylate, ethylene-ethyl acrylate, ethylene-methyl acrylate, ethylene-vinyl acetate, ethylene-vinyl acrylate, ethylene-vinyl alcohol, acrylonitrile-styrene-acrylate, styrene-acrylonitrile, styrene-maleic anhydride, meleated poly(styrene-ethylene-propylene-styrene) or meleated poly(styrene-ethylene-butylene-styrene); and in combination with or without a (V) selected amount of at least one crystalline or non-crystalline polymer or copolymer selected from the group consisting of poly(styrene-butadiene-styrene), poly(styrene-butadiene), poly(styrene-isoprene-styrene), poly(styrene-isoprene), poly(styrene-ethylene-propylene), low viscosity poly(styrene-ethylene-propylene-styrene), low viscosity poly(styrene-ethylene-butylene-styrene), poly(styrene-ethylene-butylene), meleated poly(styrene-ethylene-butylene-styrene), high vinyl content poly(styrene-ethylene-butylene-styrene), poly(styrene-ethylene-propylene-styrene-ethylene-propylene), poly(ethylene-propylene), poly(styrene-butadiene)$_n$, poly(styrene-butadiene)n, poly(styrene-isoprene)$_n$, poly(styrene-isoprene)$_n$, poly(styrene-ethylene-propylene)$_n$, low viscosity poly(styrene-ethylene-propylene)$_n$, low viscosity poly(styrene-ethylene-butylene)$_n$, poly(styrene-ethylene-butylene)$_n$, meleated poly(styrene-ethylene-butylene)$_n$, high vinyl content poly(styrene-ethylene-butylene)$_n$, poly(styrene-ethylene-propylene-styrene-ethylene-propylene)$_n$, poly(ethylene-propylene)$_n$, polystyrene, polybutylene, poly(ethylene-propylene), poly(ethylene-butylene), polypropylene, polyethylene, or polypthalamide, wherein said selected block copolymer is a linear, branched, multiarm, or star shaped copolymer.

As used herein, the term "gel rigidity" in gram Bloom is determined by the gram weight required to depress a gel a distance of 4 mm with a piston having a cross-sectional area of 1 square centimeter at 23° C.

The various types of high viscosity linear, branched, multiarm, or star shaped block copolymers employed as one or more component(s) forming the fluffy, strong, solid shape recoverable elastic gelatinous elastomer composition, $G_n$, of the invention are of the general configurations A-Z-A and (A-Z)$_n$, wherein the subscript n is two or more. In the case of multiarm block copolymers where n is 2, the block copolymer denoted by (A-Z)$_n$ is the linear block copolymer A-Z-A, for sake of simplicity the stable coupling agent residue is ignored.

The end block segment (A) comprises a glassy amorphous polymer end block segment, preferably, polystyrene and the midblocks (Z) comprises a midblock of poly(ethylene), poly(butylene), poly(ethylene-butylene), poly(ethylene-propylene) or a combination thereof.

Advantageously, $G_n$ can be made substantially more tear resistant, more resistant to high shear and high stress rupturing by selecting block copolymers with one or more substantially crystalline poly(ethylene) midblock (simply denoted by "-E- or (E)") in combination with one or more amorphous midblocks of poly(butylene), poly(ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" (when referring to one or more of the amorphous midblocks as a group) not to be confused with (Z) which denotes the midblocks (-E-, -EB-, -B-, -EP- and -W-) between the end (A) blocks. The A and Z portions are incompatible and form a two or more-phase system consisting of sub-micron amorphous glassy domains (A) interconnected by (Z) chains. The glassy domains serve to crosslink and reinforce the structure. This physical elastomeric network structure is reversible, and heating the polymer above the softening point of the glassy domains temporarily disrupt the structure, which can be restored by lowering the temperature.

The $G_n$ of the invention having one or more block copolymers with substantially crystalline polyethylene midblocks are hereafter referred to as "fluffy elastic-crystalline gels" or simpler "fluffy crystal gels". The block midblocks of copolymers forming the fluffy crystal gels are characterized by sufficient crystallinity as to exhibit a melting endotherm of at least about 40° C. as determined by DSC curve. The fluffy, elastic solid gelatinous elastomer composition of the invention made from block copolymers having substantially no crystalline polyethylene midblocks are hereafter referred to as "fluffy elastic-amorphous gels" or simpler "fluffy amorphous gels". For simplicity, the fluffy amorphous gels and fluffy crystal gels will be referred to generally as "fluffy gels" or even more simply as $G_n$ above. When referring to the gels' amorphous or crystal nature, they will be referred to as fluffy amorphous gels and fluffy crystal gels.

More surprisingly and advantageously, certain selected unique fluffy crystal gels of the invention have the unique ability to exhibit time delay complete elastic-recovery from its extended or deformed state or shape back to its original state and shape. This is attributed the block copolymer component(s) having a higher crystalline -E- segment midblock(s).

The amorphous block copolymer components are advantageously modified by the presence of the higher crystalline -E- segment(s) which may resist crazing and cavitation that immediately precedes fibrillation of the polystyrene domains due to applied stress causing catastrophic crack development and failure of the fluffy gels without adequate crystalline -E- segments.

The fluffy gels can be made in combination with a selected amount of one or more (IV) and/or (V) polymers and copolymers including thermoplastic crystalline polyurethane elastomers with hydrocarbon blocks, homopolymers, copolymers, block copolymers, polyethylene copolymers, polypropylene copolymers, and the like described below.

The high viscosity linear (I) block copolymers are characterized as having a Brookfield Viscosity value at 5 weight percent solids solution in toluene at 30° C. of from at least about 35 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The high viscosity (I) branched, star-shaped or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The high viscosity linear (I) high vinyl content SEBS block copolymers are characterized as having a Brookfield Viscosity value at 10 weight percent solids solution in toluene at 25° C. of from at least about 35 cps to about 100 cps and higher, advantageously from about 40 cps to about 80 cps and higher, more advantageously from about 50 cps to about 70 cps and higher, still more advantageously from about 50 cps to about 90 cps and higher, and even more advantageously from about 60 cps to about 100 cps and higher.

Using Toluene Viscosity at 10% solids at 25° C. of approximately 1,800 cP or the equivalent viscosity at 5 weight percent solids solution in toluene at 30° C. of approximate 40 as reference for the linear block copolymer SEBS (Kraton G 1651), the various ranges considered as high viscosities denoted above for the different block copolymers (linear, multiarm, radial, an branched block copolymers) although somewhat different are substantially comparable in molecular weights.

The various aspects and advantages of the invention will become apparent to those skilled in the art upon consideration of the accompanying disclosure and the drawings.

DESCRIPTION OF THE PREFERRED EMBODIMENTS

Extremely Light fluffy, strong, and highly elastic gel compositions are unknown in the art. The solid elastic fluffy gels employed in the present invention are different and not the same as the visco-elastic fluids or materials of patents '913 and '657. The gels of the instant invention do not exhibit the property of visco-elastic fluids and are not flowable in the ambient state, but remains substantially a elastic solid below its "A" domain's glassy disassociation temperature or melting point. In order to make strong, dimensionally stable, solid elastic oil-gels from high viscosity block copolymers, it is necessary to process the oil and high viscosity block copolymers at high temperatures above about 150° C. to about 200° C. for sufficient long times until a homogeneous molten blend is obtained. Such oil-gels can also be made using high intensity mixers for about 50 minutes at 190° C.–210° C. under vacuum. Under such process conditions, the molten oil and block copolymer gel viscosities can be quite high depending on the rate of shear. At even low shear rates, the molten block copolymer gel exhibit viscosities greatest at above about the glassy domain melting point. Even above the glassy domain melting point, the melt viscosities can be very high. As an example, the viscosity at 5% concentration in oil at 300° F. for a high viscosity poly(styrene-ethylene-butylene-styrene) block copolymer can be as high as 42,700 cps. At about slightly below the processing temperature, the molten high viscosity block copolymer gel becomes a weak solid. At about 300° F., the gel exhibit the character of a weak elastic solid. Of course, at ambient temperature, it is impossible to even incorporate a single microsphere into the gel, because the gel is solid. Consequently, incorporating even a small or moderate amount of microspheres into the molten gel at processing temperatures is difficult. It would only further greatly increase the molten gel's viscosity making it more difficult to process. The increase viscosity with each addition of microspheres makes for an impossible task to obtain a truly light weight fluffy elastic gel. Microspheres such as those made from methacrylonitrile can be easily and quickly destroyed under such long times at high process temperatures and shear above its rupture temperature $T_{max}$. Incorporation of sufficient amount of methacrylobitrile microspheres to make a light fluffy "closed cell" elastic solid gel is heretofore unrealized and unobtainable. Incorporation of even a small amounts of unexpanded methacrylonitrile microspheres is impossible due to the high molten gel viscosity and temperature conditions. Upon exposure of the unexpanded microspheres to such high process temperature, the microspheres instantly expands and became even more difficult to work into the molten gel due to the microsphere's increased size, low density in combination with the extreme high molten gel viscosity and high process temperatures.

Consequently, adding unexpanded thermoplastic microspheres such as methacrylonitrile microspheres at or near its upper temperature limits $T_{max}$, will only increase the already high viscosity of the molten oil-block copolymer gel.

The prior art ('657) did not recognize the relationship of high temperature, high molten viscosity and high block copolymer concentrations, the prior art would have had no motivation to solve the high molten viscosity problem at the high temperature process conditions; it is apparent the prior art avoided the problem by not adding any microspheres (expanded or unexpanded) at such high processing temperatures (1) by reducing the block copolymer concentration (thereby lowering the viscosity of the oil and block copolymer composition, and (2) by lowering the temperature of the polymer-oil mixture to ambient before adding any microspheres. Therefore the fluffy gels of the instant invention are not inherent in the process or the composite microsphere and lubricant mixture taught by U.S. Pat. No. 5,626,657. Clearly, heating of unexpanded thermoplastic microspheres such as methacrylonitrile microspheres at such high temperatures in a high block copolymer content/oil mixture is not taught by the prior art.

Therefore, a method I found to make a strong, fluffy, elastic solid gel having a density of at least less than 0.6 g/cm$^3$ is totally unexpected.

Expanded methacrylonitrile microspheres are not advantageous and can not be fully utilized to make the fluffy gels of the invention at the required high process temperatures; while, unexpanded methacrylonitrile microspheres will explode up to almost 50 times their volume (very much like "pop corn") when exposed to above their $T_{start}$ temperatures. The temperature at which they start expanding or popping, however, are too low (106–135° C.) to be suitable for incorporation into the high viscosity molten gel at the needed gel processing temperatures. The advantage of using unexpanded microspheres is that they can be very effective for making rapid expansive foams below their $T_{max}$ expansion temperatures provided they do not rupture. Hence, their low $T_{max}$ temperature prevent their use for foaming at the high block copolymer concentrations and high gel processing temperatures. Therefore, the low temperature properties of the unexpanded microspheres and the process conditions of the molten gel makes it impossible to make fluffy gels before the present invention.

The problem is to find ways to enable the unexpanded microspheres to be (i) added and dispersed in substantial quantities in the molten gel without substantially increasing the gel's molten viscosity, (ii) delay or retard the start of their expansion in the molten gel to allow for sufficient dispersion, (iii) limit, restrict or control their exposure the high rupture ($T_{max}$) temperatures while being dispersed in the molten gel, and (iv) adequately allowing dispersion of the microspheres particles into the molten gel.

Conventionally, in order to lower the molten gel viscosity to provide for sufficient dispersion of the microspheres, the process temperatures needs to be increased which pushes the process temperature even higher above the microsphere's rupture temperature. Whereas, attempting to maintain a sufficient low process temperature (at or below $T_{max}$) and applying high pressures will require high shear resulting uncontrollable pressure and viscosity fluctuations which will result in inadequate dispersion.

A simple solution to the critical conditions i–iv has been found to provide fluffy gels having a density of at least less than about 0.6 g/cm$^3$, more advantageously at least about 0.5 g/cm3, still more advantageously at least about 0.4 g/cm3, and still more advantageously at least about 0.3 g/cm3 or less.

Not only are fluffy gels obtained, gels which are fluffy as well as strong, highly elastic, exhibit shape-memory, resistant to tear, high shear and high stress rupturing, and exhibit controlled delay response and slow, complete recovery from extension and deformation are also obtained.

I have now discovered a method of incorporating large quantities of unexpanded microspheres, delay the microspheres' onset of expansion by controlling their exposure to high heat, thereby, allowing adequately time to disperse the microspheres particles into the molten gel. The method I found is as follows:

As a first approximation, I determine the time required for adequately mixing a selected volume or mass of molten gel as a function of temperature and molten gel viscosity. This allows for a better understanding of the mixing equipment and conditions chosen for making the fluffy gels of the invention. This can be determined for any large or medium mixing equipment used, even a small test tube.

The components I, II, IV and V of the invention blend easily in the melt and a heated vessel equipped with a stirrer is all that is required. While conventional large vessels with pressure and/or vacuum means can be utilized in forming large batches of the instant fluffy crystal gels in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher).

Simply mix a selected, predetermined amount of ingredients I and II in the chosen equipment under heat (at a constant rate of mixing) at the lowest temperature that will provide a homogenous clear, optically transparent molten gel mixture. Add a selected amount of color (e.g., orange color) polypropylene pellets and measure the time required to uniformly disperse the color pellets in the molten gel. Next, increase the temperature to decrease the molten gel viscosity and add a hand full of a different colored high density polypropylene pellets and measure the time required to uniformly dispersed the second colored pellets in the molten gel. Repeat the procedure to obtain a time-temperature-viscosity relationship graph of the time required to uniformly mix a selected volume or mass at increasing temperatures and varying viscosities of the molten gel in the chosen equipment. By this method, the time, $t_u$, required to uniformly disperse a unite volume or mass in the molten gel at any selected temperature or viscosity can be determined.

In making a fluffy gel, I need to (1) predetermine the rigidity and quantity of the final fluffy gel I wish to make, (2) estimate the final process temperature and viscosity before incorporating the unexpanded microspheres into the hot molten gel, (3) combine selected raw materials (I) and/or (IV) and (V) ingredients, and (4) add a predetermined selected amount of (II) ingredient, (5) blend together the components as desired at about 23° C. to about 100° C. forming a paste like mixture and further heating said mixture uniformly to about 150° C. to about 200° C. until a homogeneous molten blend is obtained (Lower and higher temperatures can also be utilized depending on the viscosity of the oils and amounts of block copolymers and polymer used.

With the predetermined amount of the remainder (II) ingredient, I (6) add and mix with it a selected measured quantity of (III) unexpanded microspheres at ambient temperature. The predetermined amount of (II) ingredient utilized initially to make the molten gel can range between less than about 75% to about 95% or higher (according to the criteria set out below). Depending on the final molten gel temperature, viscosity, and volume or quantity of the preselected molten gel, I set the following general guide and requirements: match the viscosity of the mixture of (II) and (III) to form a (IIIa) (unexpanded microsphere/oil) mixture with a viscosity (4b) about as close as possible matching the viscosity of the molten gel. I then estimate and select a time, $t_u$, for mixing a unit volume of the molten gel from the graph (temperature, time, viscosity and equipment relationship). Then I determined by measuring in a preheated oven (set at the same temperature as the temperature of the molten gel) the time, $t_r$, required to raise the temperature of the mass of (IIIa) from ambient to the temperature $T_{max}$. I then adjust $t_r$ by adding from the remainder ingredient (II) additional amounts to (IIIa) until the time ($t_r$) equals preferably at least about $\frac{1}{20}(t_u)$, more preferably $\frac{1}{10}(t_u)$, still more preferably about at least $\frac{1}{4}(t_u)$, and especially more preferably about at least $\frac{1}{2}(t_u)$. When the molten gel temperature is below $T_{max}$, the $t_r$ selected chosen is preferably from about less than $\frac{1}{10}(t_u)$ to about $\frac{1}{4}(t_u)$ or higher. When the molten gel temperature is above $t_{max}$, the $t_r$ selected is preferably from about less than about $\frac{1}{4}(t_u)$ to about $\frac{1}{2}(t_u)$ or higher. The reason for increasing the mass of IIIa is to prevent the temperature surrounding the microspheres to rise too quickly in the higher temperature molten gel. Hence, the greater the $t_u$ or added mass selected, the lower the viscosity and longer the time available for adequate dispersion of the unexpanded microspheres in the molten gel.

Following the criteria above, a fluffy gel can be obtained of almost any desired density. The polymers forming the gels of the invention are described and illustrate in copending application Ser. No. 863,794 and incorporated herein by reference. Theory notwithstanding, the block copolymer structures can be spheroid, cylinders, plates, and ordered bicontinuous are also within the scope of the present invention. Cylinder and plate structure are obtained with increasing glassy A end blocks. From about 15–30% by weight of A blocks, the block copolymer structure is spheroid. From about 30 about 40% by weight of A blocks, the block copolymer structure becomes cylindrical for linear block copolymers and ordered bicontinous structures (OBDD) for multi-arm block copolymers; and above about 45% A blocks, the structure becomes less cylindrical and more plate like for linear block copolymers and about 60% and higher the structure becomes OBDD for linear blocks copolymers as well.

The advantages of sufficient crystalline -E- block copolymer midblock segments for improving gel tear and stress rupturing is unknown in the art. For example, U.S. Pat. No. 5,132,355 teaches gelling liquid hydrocarbons by polyethylene block copolymers to yield pumpable hydrocarbon polymer mixtures continuing a gelling polyethylene block copolymer agent. U.S. Pat. No. 5,276,100 disclose solid block copolymers having improved resistance to clod flow. Other patents such as U.S. Pat. Nos. 5,571,864 and 5,654,364 are directed to miscible polyolefin blends with modifying polyolefin having matching segment lengths and miscible blend of polyolefin and polyolefin block copolymer. These patents are incorporated herein by reference.

Block copolymers containing high butylene midblock segments or substantially equal segment lengths of ethylene and butylene or ethylene and propylene are highly amorphous and are suitable for making fluffy amorphous gels of the invention, but such fluffy gels are generally weaker (with respect to tear, stress, rupture, and fatigue resistance) than crystal gels of the invention.

In order to obtain fluffy elastic crystal gels, however, it is necessary that the selective synthesis of butadiene produce sufficient amounts of 1,4 poly(butadiene) that on hydrogenation can exhibit "crystallinity" in the midblocks. In order for the block copolymers forming the fluffy crystal gels of the invention to exhibit crystallinity, the crystalline midblock segments must contain long runs of —$CH_2$— groups. There should be approximately at least 16 units of —($CH_2$)— in sequence for crystallinity. Only the (—$CH_2$—)$_4$ units can crystallize, and then only if there are at least 4 units of (—$CH_2$—)$_4$ in sequence; alternatively, the polyethylene units are denoted by [—($CH_2$—$CH_2$—$CH_2$—$CH_2$)—]$_4$, [(—$CH_2$—)$_4$]$^4$ or (—$CH_2$—)$^{16}$. The amount of (—CH2—)$^{16}$ units forming the (E) midblocks of the block copolymers comprising the fluffy crystal gels of the invention should be at least about 20% which amount is capable of exhibiting a melting endotherm in differential scanning calorimeter (DCS) curves.

Advantageously, the elastomer midblock segment should have a crystallinity of at least about 20% of (—$CH_2$—)$^{16}$ units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks should range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The maximum in the endotherm curves of the crystalline block copolymers occurs at about 40° C., but can range from greater than about 25° C. to about 60° C. and higher. The crystalline block copolymers forming the fluffy crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., 120° C., and higher, whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DCS curves of amorphous gels. The crystallization exotherm and fusion endortherm of the crystalline block copolymer gels of the invention are determined by ASTM D 3417 method.

Generally, the method of obtaining long runs of crystalline —($CH_2$)— is by sequential block copolymer synthesis followed by hydrogenation. The attainment of fluffy crystal gels of the instant invention is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalline midblocks of the final block copolymers.

The crystalline block copolymers are made by sequential block copolymer synthesis, the percentage of crystallinity or $(-CH_2-)_{16}$ units should be at least about $(0.67)^4$ or about 20% and actual crystallinity of about 12%. For example, a selectively synthesized S-$EB_n$-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of $(-CH2-)_4$ units, e.g., n=33 or 20% crystallinity which is the percentage of $(0.67)^4$ or "$(-CH_2-)_{16}$" units. Thus, when n=28 or 72% of $(-CH_2-)_4$ units, the % crystallinity is $(0.72)^4$ or 26.87% crystallinity attributed to $(-CH_2-)_{16}$ units, denoted by -$EB_{28}$-. As a matter of convention, and for purposes of this specification involving hydrogenated polybutadiene: the notation -E- denotes at least about 85% of $(-CH_2-)_4$ units. The notation -B- denotes at least about 70% of $[-CH_2-CH(C_2H_5)-]$ units. The notation -EB- denotes between about 15 and 70% $[-CH_2-CH(C_2H_5)-]$ units. The notation -$EB_n$- denotes n % $[-CH_2-CH(C_2H_5)-]$ units. For hydrogenated polyisoprene: The notation -EP- denotes about at least 90% $[-CH_2-CH(CH_3)-CH_2-CH_2-]$ units.

Likewise, in order to obtain the highly amorphous midblock components such as -B- forming the fluffy amorphous gels, it is necessary that the selective synthesis of butadiene produce sufficient amounts of vinyl or 1,2 poly(butadiene) that on hydrogenation can exhibit "substantially amorphous polybutene" midblocks. The notation -B- denotes greater than above about 70% $[-CH2-CH(C2H5)-]n$ polybutene units and -P- denotes greater than 70% $[-CH(CH-2CH3)-CH2-]_n$ polyisopropylethyene units. The substantially amorphous midblocks -$EB_n$- and -$EP_n$- of $SEB_nS$ and $SEP_nS$ (or more simply denoted when n % is greater than about 70% as -B- and -P-) are more advantageously when n % is greater than about 75%, still more advantageously greater than about 80%, and still more advantageously greater than about 85%, and even still more advantageously greater than about 90% or higher. Typically, high polybutene content $SEB_nS$ or simply SBS is made by adding structure modifiers, such as ethers, which gives more 1,2 polybutadiene and after hydrogenation, more polybutene, resulting in less crystallinity, softer block copolymer, lower viscosity, and higher $T_g$. Likewise, high polyisopropylethyene content $SEP_nS$ or simply S-P-S is made by adding structure modifiers to give more 3,4 structure and after hydrogenation, more polyisopropylethyene, resulting in softer block copolymer, lower viscosity, and higher $T_g$.

The major advantages of $SEB_nS$ and $SEP_nS$ over SEBS, SEPS (when n %=greater than about 70%) is the $T_g$ of poly(styrene-ethylene-butylene$_{>70}$-styrene) and poly(styrene-ethylene/propylene-isopropylethyene$_{>70}$-styrene) are much higher; the gel rigidities are lower; and the viscosities are much lower. More specifically, the Tg of SEBS is typically about −58° C. and the Tg of SEPS is typically about −50 to about −60° C. Whereas, the Tg of $SEB_nS$ and $SEP_nS$ with high butylene content and high isopropylethyene content can be advantageously much higher of about less than about −40° C., advantageously −30° C. and more advantageously higher of about −27° C. and higher.

It is extraordinary that where typical SEBS and SEPS fluffy amorphous gels fails to provide greater tensile strength, fails to provide greater tear strength, and fails to provide greater resistance to high stress rupture, hereto unknown and unappreciated modification of the midblock structures provide heretofore unrealizable improved higher tensile strength, improved higher tear strength, and improved higher resistance to high stress rupture.

Theory notwithstanding, SEBS and SEPS or fluffy amorphous gels fail to provide greater improved properties. The following is known:

i) fluffy amorphous gels made from typical SEBS which is created from a mixture of 1, 4- and 1,2-polybutadiene to provide a random mixture of ethylene and butylene units greater to suppress crystallinity (as noted by Legge). Such fluffy amorphous gels can not provide greater tear strength and lack greater resistance to high stress rupture.

ii) fluffy amorphous gels made from typical SEPS which is created by hydrogenation of cis-1,4-polyisoprene results in a 1:1 ethylene/propylene elastomer midblock (as noted by Legge). Such fluffy amorphous gels can not provide greater tear strength and lack greater resistance to high stress rupture.

Contrary to the inferior properties of the above fluffy amorphous gels 1) and 2), the following fluffy crystal gels are found to be superior and of improved high tear strength, improved resistance to high stress rupture and sufficient greater tensile strength:

iii) fluffy crystal gels made from an admixture of a high crystalline ethylene content S-$E_n$B-S block copolymer and a high butylene content S-$EB_n$-S block copolymer.

iv) fluffy crystal gels made from an admixture of a high crystalline ethylene content S-$E_n$B-S block copolymer and a high polyisopropylethyene content S-$EP_n$-S block copolymer.

v) fluffy crystal gels made from an admixture of a high crystalline ethylene content S-$E_n$B-S block copolymer, a high butylene content S-$EB_n$-S block copolymer, and a high polyisopropylethyene content S-$EP_n$-S block copolymer vi) S-E-$EB_{>70}$-E-S fluffy crystal gels made by coupling S-E-$EB_{>70}$.

vii) S-E-$EP_{>70}$-E-S fluffy crystal gels made by coupling S-E-$EP_{>70}$.

viii) fluffy crystal gels made from linear, branched, radial, star-shaped, multi-arm or branched block copolymers having sufficient multiple midblock components of high crystalline ethylene content, high butylene content, and/or high isopropylethyene content including all combinations, sequential additions and permutations and mixtures of such block copolymers and as described herein are of the greatest advantage.

Generally, one or more (E) midblocks can be incorporated at various positions along the midblocks of the block copolymers. Using the sequential process for block copolymer synthesis, The (E) midblocks can be positioned as follows:

| | |
|---|---|
| i) A-E-W-A | ii) A-E-W-E-A |
| ii) A-W-E-W-A | iii) A-E-W-E-W-E-W-E-A |
| iv) A-W-E-W-A-E-A-E-W-E-A | v) A-W-A |
| vi) A-E-A, etc. | |

The lower flexibility of the block copolymer fluffy crystal gels due to high (E) content midblocks can be balanced by the addition of sequentially formed (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, (S-EP)$_n$ and the like can produce more softer, less rigid, and more flexible fluffy crystal gel.

In additional to the block copolymers S-E-EB-S and S-E-EP-S, such other block copolymers such as, for example, S-E-EB-E-S can be made by coupling S-E-EB and S-E-EP-E-S can be made by coupling S-E-EP or by making it sequentially. Multi-arm of such block copolymers can also be made.

Because of the (E) midblocks, the fluffy crystal gels of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the fluffy crystal gels when stretched exhibit additional yielding as shown by necking caused by stress induced crystallinity. Additionally, the crystallization rates of the crystalline midblocks can be controlled and slowed depending on thermal history producing time delay recovery upon deformation. Gels exhibiting time delay recovery following deformation is of great advantage and an improvement over fluffy amorphous gels and fluffy crystal gels for certain uses.

Gels having such time delay recovery properties are unique. Such gels of the invention can achieve delay times of from about less than 2 seconds to about 20 seconds or more. Characteristic delay times that can be achieved are from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 120, seconds and longer. Consequentially, the recovery characteristics of the time delay fluffy gels are due to the stress induced crystallization of the block copolymers used.

Surprisingly, linear, multiarm, radial, or branched block copolymers when formed into gels which exhibit such time delay behavior always have crystalline -E- component in their midblocks and are characterized as having a Brookfield Viscosity value at 5 weight percent solids solution in toluene at 30° C. of from about 120 cps to about 350 cps and higher, advantageously from about 130 cps to about 260 cps and higher, more advantageously from about 180 cps to about 380 cps and higher, and still more advantageously from about 200 cps to about 800 cps and higher. Additionally, the onset of this strange behavior is observed after the molten gel is allowed to remained undisturbed or unstirred for a selected amount of time before forming into shaped articles. It appears that crystallinity, extreme viscosities, cooling, heating and/or shear histories of the molten gels affects the onset of the time delay behavior of the room temperature gels.

Regarding the great advantage of the fluffy crystal gels' resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of fluffy amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of —CH$_2$— groups and negligible crystallinity, ie, about $(0.5)^4$ or 0.06 or 6% and actual crystallinity of about 3%. Due to the constraints of T$_g$ and minimum hysteresis, conventional S-EB-S have ethylene-butylene ratios of about 60:40 with a crystallinity of about $(0.6)^4$ or 0.129 or 12% and actual crystallinity of about 7.7%.

Block copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —CH$_2$— and no crystallinity.

Mixed block copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)^4$ or 5.3%. The actual crystallinity would be approximately about 3.2%, which is negligible and results in a good rubbery midblock.

For purpose of convince and simplicity, the hydrogenated polybutadiene are denoted as follows: -E- denotes at least 85% R-1 units, -B- denotes at least 70% R-2 units, -EB- denotes between 15 and 70% R-2 units, -EB$_n$- denotes n % R-2 units, and -EP- denotes 90% R-3 units.

Table I below gives the % of units on hydrogenation of polybutadiene/polyisoprene copolymer midblocks, where n is the mole % polybutadiene in the polybutadiene-polyisoprene starting polymer

| n = | R-1 | R-2 | R-3 | R-4 |
|---|---|---|---|---|
| 0% | 0% | 0% | 95% | 5% |
| 20% | 18% | 2% | 76% | 4% |
| 40% | 36% | 4% | 57% | 3% |
| 60% | 54% | 6% | 38% | 2% |
| 80% | 72% | 8% | 19% | 1% |
| 100% | 90% | 10% | 0% | 0% | where R-1 denotes

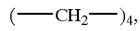

R-2 denotes

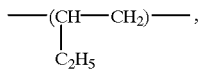

R-3 denotes

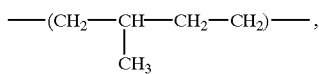

R-4 denotes

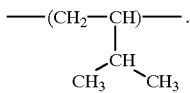

Therefore, the percentage that can crystallize is $[(-CH_2-)_4]^4$ since this is the chance of getting four $(-CH_2-)_4$ units in sequence. The percentage that will crystallize is about 60% of this.

| n = | $(-CH_2-)_4$ | $[(-CH_2-)_4]^4$ | $0.6 \times [(-CH_2-)_4]^4$ |
|---|---|---|---|
| 0% | 0% | 0% | 0% |
| 20% | 18% | 0.1% | 0.06% |
| 40% | 36% | 1.7% | 1.0% |
| 60% | 54% | 8.5% | 5.1% |
| 80% | 72% | 26.9% | 16.1% |
| 100% | 90% | 65.6% | 39.4% |

This applies to polymerization in a hydrocarbon solvent. In an ether (e.g., diethylether), the percentage $(-CH_2-)^4$ units will be reduced so that crystallinity will be negligible.

| n = | $(-CH_2-)_4$ | $[(-CH_2-)_4]^4$ | $0.6 \times [(-CH_2-)_4]^4$ |
|---|---|---|---|
| 0% | 0% | 0% | 0% |
| 20% | 5% | 0.0006% | 0.0004% |
| 40% | 10% | 0.01% | 0.006% |
| 60% | 15% | 0.05% | 0.03% |
| 80% | 20% | 0.16% | 0.10% |
| 100% | 25% | 0.39% | 0.23% |

These values are all negligible. There will be no detectable crystallinity in any of these polymer midblocks. In a mixed ether/hydrocarbon solvent, values will be intermediate, depending on the ratio of ether to hydrocarbon.

The midblocks (Z) of one or more -E-, -B-, -EB-, or -EP- can comprise various combinations of midblocks between the selected end blocks (A); these include: -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E-EP-EB-, -E-EP-E-EP-E-, -E-EP-EB-EP-EB-B- and the like.

The block copolymers of (A-Z-A) can be obtained by sequential synthesis methods followed by hydrogenation of the midblocks. As denoted above, abbreviations are interchangeably used, for example, (S-E-EP-S) denotes poly(styrene-ethylene-ethylene-co-propylene-styrene). Other linear block copolymers (denoted in abbreviations) include the following: (S-E-S), (S-Butylene-S), (S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S), (S-E-EP-E-EP-S), (S-E-EP-E-EB-S), (S-EP-B-EP-S), (S-B-EB-B-EB-S), (S-B-EB-B-EP-S), (S-E-EB-B-EP-S), (S-E-EP-B-EB-S), (S-E-EP-E-EP-E-S), (S-B-EP-B-EP-B-S), (S-E-EP-E-EB-S), (S-E-EP-E-EP-EB-S), (S-E-EP-E-EP-E-S), (S-E-EP-EB-EP-EB-B-S), (S-E-EP-E-EP-E-S), (S-E-EP-EB-EP-EB-S), (S-E-EP-EB-EP-EB . . . -S) and the like.

The multiblock star-shaped (or radial) copolymers $(A-Z)_n$ X can be obtained by sequential synthesis methods including hydrogenation of selected block copolymers made by polymerizing half of the block copolymers such as SBS or SIS and couple the halves with a coupling agent such as an organic dihalide; or couple with an agent such as SnCl4, which results in star-shaped block copolymers (four branches). Coupling with divinyl benzene give block copolymers which are very highly branched. Radial block copolymers suitable for use in forming the fluffy crystal gels of the present invention include: $(S-E)_n$, $(S-E-EB)_n$, $(S-E-EP)_n$, $(S-B-EP)_n$, $(S-B-EB)_n$, $(S-E-EP-E)_n$, $(S-E-EB-B)_n$, $(S-B-EP-B)_n$, $(S-B-EB-B)_n$, $(S-E-B-EB)_n$, $(S-E-B-EP)_n$, $(S-EB-EP)_n$, $(S-E-EB-EP)_n$, $(S-E-EP-EB)_n$, $(S-B-EB-EP)_n$, $(S-B-EP-EB)_n$, $(S-E-EP-E-EP)_n$, $(S-E-EP-E-EB)_n$, $(S-EP-B-EP)_n$, $(S-B-EB-B-EB)_n$, $(S-B-EB-B-EP)_n$, $(S-E-EB-B-EP)_n$, $(S-E-EP-B-EB)_n$, $(S-E-EP-E-EP-E)_n$, $(S-B-EP-B-EP-B)_n$, $(S-E-EP-E-EB)_n$, $(S-E-EP-E-EP-EB)_n$, $(S-E-EP-E-EP-E)_n$, $(S-E-EP-EB-EP-EB-B)_n$ and counter part multifunctional block copolymers: $(R)_n$-E-S, $(R)_n$-E-EB-S, $(R)_n$-E-EP-S, $(R)_n$-E-EP-E-S, $(R)_n$-E-EB-B-S, $(R)_n$-E-B-EB-S, $(R)_n$-E-B-EP-S, $(R)_n$-E-EB-B-EP-S, $(R)_n$-E-EP-EB-S, $(R)_n$-E-EP-E-EP-S, $(R)_n$-E-EP-E-EB-S, $(R)_n$-E-EB-B-EP-S, $(R)_n$-E-EP-B-EB-S, $(R)_n$-E-EP-E-EP-E-S, $(R)_n$-E-EP-E-EB-S, $(R)_n$-E-EP-E-EP-EB-S, $(R)_n$-E-EP-E-EP-E-S, $(R)_n$-E-EP-EB-EP-EB-B-S, $(R)_n$-E-EP-EB-EP-EB . . . -S, and the like. In the above notation, "-E-" denotes substantially crystalline polyethylene midblock.

The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of fluffy crystal gel composites, such as between the surfaces of the fluffy crystal gel and substrate or at the interfaces of the interlocking material(s) and fluffy crystal gel, which improvements are not found in amorphous gels at corresponding gel rigidities.

Selected linear block and radial copolymers utilized in forming the fluffy crystal gels of the invention are characterized as having an ethylene to butylene midblock ratio (E:B), an ethylene to ethylene/propylene (E:EP) ratio, and an ethylene to ethylene/butylene (E:EB) ratio of about 85:15 to about 65:35. Advantageously, the butylene concentration of the midblock is about 35% or less, more advantageously, about 30% or less, still more advantageously, about 25% or less, especially advantageously, about 20% or less.

Advantageously, the ethylene to butylene midblock ratios can range from about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming fluffy crystal gels of the invention can range from about 20:80 to 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and 52:48.

As described above, the $G_n$ can also be made with or without a (IV) selected minor amount (from about less than 0.5% to about 10% or more) of at least one polar polymer components such as copolymer selected from the group consisting of ethylene-butyl acrylate, ethylene-ethyl acrylate, ethylene-methyl acrylate, ethylene-vinyl acetate, ethylene-vinyl acrylate, ethylene-vinyl alcohol, acrylonitrile-styrene-acrylate, styrene-acrylonitrile, styrene-maleic anhydride, meleated poly(styrene-ethylene-propylene-styrene) or meleated poly(styrene-ethylene-butylene-styrene) and the like. Such polar components are more compatible with the polar thermoplastic microspheres as well as compatible with the non-polar components of the block copolymers forming the fluffy gels of the invention. Such polar additives can counteract to some degree the lowering of the physical properties due to increasing amounts of microsphere needed to achieve lower densities of the fluffy gels.

The fluffy gels can comprise selected major or minor amounts of one or more additional crystalline or non-crystalline polymers or copolymers (V) described above, provided the amounts and combinations are selected do not substantially decreasing the desired properties. Such V components also include polyethyleneoxide (EO), poly (dimethylphenylene oxide), teflon, optical clear amorphous copolymers based on 2,2-bistrifluoromethyl-4,5-difuoro-1, 3-dioxole (PDD) and tetrafluoroethylene (TFE) and the like. Still, other (V) polymers include homopolymers which can be utilized in minor amounts; these include: polystyrene, polydimethylsiloxane, polyolefins such as polybutylene, polyethylene, polyethylene copolymers, polypropylene and the like. Polyurethane elastomers based on saturated hydrocarbon diols (Handlin, D., Chin. S., and Masse. M., et al. "POLYURETHANE ELASTOMERS BASED ON NEW SATURATED HYDROCARBON DIOLS" Published Society of Plastics Industry, Polyurethane Division, Las Vegas, Oct. 23, 1996) are also suitable for use in blending with the block copolymers (I) used in forming the fluffy crystal gels of the invention. Such saturated hydrocarbon diols include hydroxyl terminated oligomers of poly(ethylene-butylene) (EB), poly(ethylene-propylene) (EP),-E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E-EP-EB-, -E-EP-E-EP-E-, -E-EP-EB-EP-EB- and the like. As an example, thermoplastic polyurethane (TPU) made with diisocyanates and chain extenders such as 2,2,4-trimethyl-1,3-pentancdiol (TMPD) and 2-Butyl-2-ethyl-1,3-pentanediol (BEPD) from saturated hydrocarbon diol KLP L-2203 having a hard segment contents of 22% exhibits clean phase separation of the hard and soft segments with a glass transition of −50° C. TPU polyurethane elastomers based on KLP L-2203 diol, MDI with TMPM and BEPD chain extenders at 22% hard segment, 104 isocyanate index, and cured at 105° C. gives 2,430 and 1,160 tensile psi, 1040% and 2180% elongation at break, and modulus at 300% elongation of 670 and 290 psi respectively by the one shot method. Polyurethane elastomers prepared by the one shot method based on KLP L-2203, MDI and TMP at 1.04 NCO/OH ratio having hard segment concentrations of 22%, 33% and 44% give tensiles of 2430, 2830 and 2760 psi respectively, elongations at break of 1040%, 830%, and 760% respectively, and modulus at 300% elongation of 670, 1160 and 1360 psi respectively. KLP L-2203 (hydroxyl terminated poly(ethylene-butylene) oligomer (50,000 cps at 20° C.) based TPU's can be mixed with the crystalline block copolymers to form soft fluffy crystal gels within the gel rigidity ranges of the invention. The thermoplastic crystalline triblock and multiblock polyurethane elastomers can also be blended by themselves with components II and III to make strong, elastic fluffy gels of the invention. Hence, thermoplastic polyurethanes with hard segment contents of form about less than 22% to about 45% and higher are of great advantage in forming the fluffy gels of the invention.

Suitable V components for use in the present invention include polyolefins (polyethylene and polyethylene copolymers), such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141--XT, 1430, 1420, 1320, 3330, 3150, 2912, 3340, 3460; Dow Attane (ultra low density ethylene-octene-1 copolymers) 4803, 4801, 4602 and the like. Polyolefins such as these (in minor amounts) can improve the tear and rupture resistance of the compositions of the invention due to their crystalline contributions.

The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Additional example of polymers, copolymers, and blends include: (a) Kraton G 1651, G 1654X; (b) Kraton G 4600; (c) Kraton G 4609; other suitable high viscosity polymer and oils include: (d) Tuftec H 1051; (e) Tuftec H 1041; (f) Tuftec H 1052; (g) Kuraray SEPS 4033; (h) Kuraray S-EB-S 8006; (i) Kuraray SEPS 2005; (j) Kuraray SEPS 2006, and (k) blends (polyblends) of (a)–(h) with other polymers and copolymers include: (1) S-EB-S/SBS; (2) S-EB-S/SIS; (3) S-EB-S/(SEP); (4) S-EB-S/(SEB)$_n$; (5) S-EB-S/(SEB)$_n$; (6) S-EB-S/(SEP)$_n$; (7) S-EB-S/(SI)$_n$; (8) S-EB-S/(SI) multi-arm; (9) S-EB-S/(SEB)$_n$; (10) (SEB)$_n$ star-shaped copolymer; (11) s made from blends of (a)–(k) with other homopolymers include: (12) S-EB-S/polystyrene; (13) S-EB-S/polybutylene; (14) S-EB-S/poly-ethylene; (14) S-EB-S/polypropylene; (16) SEP/S-EB-S, (17) SEP/SEPS, (18) SEP/SEPS/SEB, (19), SEPS/S-EB-S/SEP, (20), SEB/S-EB-S (21), EB-EP/S-EB-S (22), S-EB-S/EB (23), S-EB-S/EP (24), (25) (SEB)$_n$ s, (26) (SEP)$_n$, (27) Kuraray 2007 (SEPS), (28) Kuraray 2002, (SEPS), (29) Kuraray 4055 (S-EB-EP-S) (30) Kuraray 4077 (S-EB-EP-S) (31) Kuraray 4045 (S-EB-EP-S) (32) (S-EB-EP)$_n$, (33) (SEB)$_n$, (34) EPDM, (35) EPR, (36) EVA, (37) coPP, (38) EMA, (39) EEA, (40) DuPont Teflon AF amorphous fluoropolymers, (41) Dow polydimethylsiloxane, (42) maleated S-EB-S (maleation level 2–30%), (43) (EP)$_n$, GRP-6918 (SEPS), G1730 (SEPSEP), G1780 (SEP)n, GRP-6906 (SEPS), GRP-6917 (SEBS), KX-219, KX-222, KX-605, RP-6919 (SEBIS) and the like.

Representative examples of commercial elastomers that can be combined with the block copolymers (I) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1650, G1651, G1652, G4609, G4600, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, G1730M, FG1901X and FG1921X. Kuraray's SEP, SEPS, S-EB-S, S-EB-EP-S Nos. 1001, 1050, 2027, 2003, 2006, 2007, 2008, 2023, 2043, 2063, 2050, 2103, 2104, 2105, 4033, 4045, 4055, 4077, 8004, 8006, 8007, H-VS-3 (S-V-EP)n, Kraton G 1901, 1921, 1924 and the like.

The block copolymers can have a broad range of styrene to ethylene-butylene ratios (S:EB) and styrene to ethylene-propylene ratios (S:EP) of about 20:80 or less to about 40:60 or higher. The S:EB weight ratios can range from lower than about 20:80 to above about 40:60 and higher.

The Brookfield Viscosity of a 5 weight percent solids solution in toluene at 30° C. of 2006, 4045, 4055, 4077 typically range about 20–35, about 25–150, about 60–150, about 200–400 respectively. Typical Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable block copolymers and their typical viscosities are further described. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68-79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of S-EB-S, SEPS, $(SEB)_n$, $(SEP)_n$ polymers can also be utilized in the present invention provided such polymers exhibits the required high viscosity. Such S-EB-S polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:EB-EP) ratios of Kuraray's SEPTON 4045, 4055, and 4077 are typically about 37.6, 30, 30 respectively. More typically the (S:EB-EP) and (S:EP) ratios can vary broadly much like S:EB ratios of S-EB-S and $(SEB)_n$ from less than 19:81 to higher than 51:49 (as recited above) are possible. It should be noted that multiblock copolymers including SEPTON 4045, 4055, 4077 and the like are described in my cited copending parent applications and are the subject matter of related inventions.

The block copolymers such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers (II) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

The amount of plasticizing oil (II) sufficient to achieve gel rigidities of from less than about 2 gram Bloom to about 3,000 gram Bloom range from less than about 250 to about 2,000 parts by weight of a plasticizing oil.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene-butylene-styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton KLP L-2203 and Kraton KLP L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, Witco brand white oils including RR-654-P and the like. Generally, plasticizing oils with average molecular weights less than about 200 and greater than about 700 may also be used (e.g., H-300 (1290 Mn)).

Comparisons of oil extended S-EB-S triblock copolymers have been described in Shell Chemical Company Technical Bulletin SC:1102-89 (April 1989) "KRATON® THERMOPLASTIC RUBBERS IN OIL GELS" which is incorporated herein by reference.

Of great advantage are the unexpanded particulate materials which can be dispersed and within a controlled temperature heating range can produce a predetermined volume of closed cell particulate dispersions forming the fluffy gels. The particulate materials useful are unexpanded microspheres of poly(acrylonitrile-methacrylonitrile) copolymers encapsulated liquid isopentane which are available from Akzo Nobel by the tradename Expancel. The thermoplastic microspheres comprises at least about 80% weight of copolymer and about 6 to about 16% isopentane and are further characterized as having a unexpanded relative density of about 1.2 ($H_2O$=1.0), particle size of about 3 to about 50 microns, a $T_{start}$ or softing temperature of about 106° C. to about 135° C. and a decomposition or rupturing temperature $T_{max}$ of about 138° C. to about 195° C. The unexpanded thermoplastic microspheres are activated by heat and expand to approximately about 50 times its unexpanded size to provide an average particle density of about less than 0.020 specific gravity. Their lowest calculated density reached at $T_{max}$ during TMA test is between about 0.25 to about 0.017 g/cm$^3$. More specifically, unexpanded grades of microspheres include grades followed by (range of temperatures $T_{start}$° C./$T_{max}$° C.): #051 (106-111/138-147), #053 (95-102/137-145), #054 (125-135/140/150), #091 (118-126/161-171), #091-80 (118-126/171-181), and #092-120 (118-126/185-195). Other expandable thermoplastic microspheres can be of advantage in making the fluffy gels of the invention. Such should be of higher temperature activated unexpanded thermoplastic microspheres with liquid isopentane, isobutane cores, and the like. Suitably higher $T_{start}$ and $T_{max}$ temperature unexpanded thermoplastic microspheres contemplated for use in the present invention can have ($T_{start}$/$T_{max}$) of about (110° C./200° C.), (100° C./205° C.), (100° C./210° C.), (100° C./215° C.), (100° C./220° C.). (100° C./225° C.), (100° C./230° C.), (100° C./235° C.) and higher.

Fluffy gels of the invention of densities of about 0.6 g/cm$^3$ comprises about at least above about 5%–6% by weight of unexpanded microspheres, at about 0.5 g/cm$^3$, the amount of microspheres is approximately about 10%–11% by weight, at about 0.4 g/cm$^3$, the amount of microspheres is about 12%–15%, and at about 0.3 g/cm$^3$, the amount of microspheres is about 18%–20% or higher. Higher density gels (about 0.7 g/cm$^3$ and about 0.8 g/cm$^3$) can also be made following the teachings of the present invention. Suitable amounts of unexpanded microspheres useful in forming the fluffy gels of the invention can range from about less than 5% to 30% or higher, more suitably, from about 5% to 25% or higher, and still more suitably, from about 5% to about 20% or higher. As the densities of the fluffy gels of the invention is made less and less, the physical properties of the fluffy gels also are more and more affected. The fluffy crystal gel physical properties remain substantially higher than the physical properties of the fluffy amorphous gels of the invention. This is due to the crystalline contributions as described earlier.

Microspheres incapable of softing by heat and therefore are unexpandable or remains unexpanded, such as phenolic microspheres are not suitable for making the fluffy gels of the present invention because phenolic, a heat-cured thermoset, is the reaction product of phenol and formaldehyde and the structured formed gives it heat resistance, dimensional stability, creep resistance and hardness. Likewise glass microspheres, metal, quartz and carbon microspheres and the like are not suitable for use in the present invention.

Accordingly, a selected amount of one or more of the heat activated unexpanded thermoplastic particulate materials are dispersed in an ordered, random, homogeneous, nonhomogeneous, stratified, partially stratified or one or more separated phases. The dispersed unexpanded particulate materials are capable of producing a predetermined volume of closed cell particulate dispersion forming the fluffy gels with densities of at least less than about 0.60 g/cm3. The fluffy gels further having a gel rigidity of from about 20 to about 3,000 gram Bloom, and an elongation of at least 200%. Typical densities which can be achieved can range from greater than about 0.6 g/cm3 to less that about 0.3 g/cm3. Fluffy gel densities of about 0.75, 0.70, 0.65, 0.60, 0.55, 0.50, 0.45, 0.40, 0.35, 0.30 or lower can be achieved using the unexpanded particulate materials.

The fluffy gels can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of S-EB-S (a ratio of 0.1) will result in spotted tack reduction on the surface of the gel. A ratio of 250 to 2,000 will result in spotted crystallized stearic acid regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of S-EB-S. The same excellent result is achieved when S-EB-S is adjusted to 3,000 grams, 4,000 grams, etc. The same result is achieved with (I) copolymers as well as in combination with polymers (II) such as SEPS, S-EB-EP-S, (S-EB-EP)$_n$, (SEB)$_n$, (SEP)$_n$ polymers. Moreover, when about 50 grams of tetrakis [methylene 3,-(3'5'-di-tertbutyl-4"-hydroxyphenyl) propionate] methane is use as a tack reducing blooming agent, tack is completely removed from the surface of the gel after two to three weeks of blooming.

The fluffy crystal gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives in varying amounts useful in the gels of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl-pentaerythritol-diprophionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g., polyethylene, polypropylene, microcrystalline, carnauba, paraffin, montan, candelilla, beeswax, ozokerite, ceresine, and the like), teflon (TFE, PTFE, PEA, FEP, etc), polysiloxane, etc. The fluffy crystal gel can also contain metallic pigments (aluminum and brass flakes), TiO2, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicones, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The fluffy gels can also be made into composites. The gels can be casted unto, pressured molded, injection molded and various methods of forming with or interlocking with various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten crystal gel is deformed as it is being cooled. Useful open-cell plastics include: polyamides, polyimides, polyesters, polyisocyanurates, polyisocyanates, polyurethanes, poly (vinyl alcohol), etc. Suitable open-celled Plastic (sponges) are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The $G_n$ can also be formed with or physically interlocked with a selected material $M_n$ to form a composite comprising combinations of $G_n$ and $M_n$, any sequential additions or permutations of said combinations $M_nG_n$, $G_nM_nG_n$, $M_nG_nM_n$, $M_nG_nG_n$, $M_nM_nG_n$, $M_nG_nG_nG_n$, $M_nM_nM_nG_n$, including $M_nG_nG_nM_n$, $G_nM_nG_nM_n$, $G_nG_nM_nG_n$, $M_nG_nM_nM_n$, $M_nG_nM_nG_n$, $G_nM_nG_nG_n$, $G_nM_nM_nG_n$, $G_nG_nM_nM_n$, $G_nG_nM_nG_nM_n$, $G_nM_nG_nM_nM_n$, $G_nM_nG_nM_nG_n$, $G_nM_nM_nG_nG_n$, $G_nG_nG_nM_nM_n$, $M_nG_nG_nM_nG_n$, $M_nG_nM_nG_nM_n$, $G_nG_nM_nM_nM_n$, $G_nM_nM_nG_nG_n$, $M_nG_nM_nG_nG_n$, $M_nG_nG_nM_nM_nG_n$, $G_nG_nM_nG_nG_nG_n$, $M_nG_nM_nG_nM_nG_n$, $G_nM_nM_nG_nM_nG_n$, $G_nG_nM_nM_nG_nM_n$, $G_nM_nM_nG_nG_nM_n$, $M_nM_nG_nG_nM_nM_n$, $M_nG_nG_nM_nG_nM_n$, $M_nG_nG_nM_nG_nG_n$, $G_nG_nM_nG_nG_nM_n$, $G_nM_nG_nM_nG_n$, $M_nM_nM_nG_nM_nM_nM_n$ $M_nG_nM_nG_nG_nM_n$,    $G_nM_nG_nM_nG_nM_nG_n$, $M_nG_nM_nG_nM_nM_nG_n$,    $G_nM_nM_nG_nM_nM_nG_n$, $M_nG_nG_nM_nG_nG_nM_n$, $G_nM_nG_nM_nG_nM_nG_nM_n$, $G_nG_nM_nM_nG_nG_nM_nM_n$, $G_nG_nM_nG_nG_nM_nG_nG_n$, $M_nG_nG_nM_nG_nG_nM_n$, $G_nM_nG_nG_nM_nG_nG_nM_nG_n$, $G_nG_nM_nG_nM_nG_nM_nG_n$, or $G_nM_nG_nM_nG_nM_nG_nG_nM_nG_nM_nG_nM_nG_n$, wherein when n is a subscript of M, n is the same or different selected from the group consisting of foam, plastic, fabric, metal, concrete, wood, glass, ceramics, synthetic resin, synthetic fibers or refractory materials. The fluffy crystal gels of the composites are formed from components (I), (II), (III), and/or (IV) or (V) described above.

Sandwiches of fluffy gel-material, fluffy gel-material-fluffy gel or material-fluffy gel-material are useful as shock absorbers, acoustical isolators, vibration dampers, vibration isolators, and wrappers. For example the vibration isolators can be use under research microscopes, office equipment, tables, and the like to remove background vibrations. The tear resistance nature of the instant fluffy crystal gels are superior in performance to fluffy amorphous gels which are much less resistance to crack propagation caused by long term continue dynamic loadings.

The fluffy gel articles can be formed by blending, injection molding, extruding, spinning, casting, dipping and other conventional methods. For example, Shapes having various cross-section can be extruded. The fluffy crystal gels can also be formed directly into articles or remelted in any suitable hot melt applicator and extruded into shaped articles and films or spun into threads, strips, bands, yarns, or other shapes.

The fluffy gels are excellent for cast, injection, or spinning molding and the molded products have high tear resistance characteristics which cannot be anticipated form the properties of the raw components. Other conventional methods of forming the composition can be utilized.

It is found that orientation substantially affects the properties of the fluffy gels as well as non-fluffy gels made from the (I) copolymers of the invention. A non-fluffy gel is a gel which is void of the microsphere particulate dispersion of the fluffy gels. In other words a plain optically clear gel. The effect of orientation is noted as follows: when a optically clear gel is extruded by conventional means, such as under high pressure or experience extreme high tension and extension while being rapidly cooled, the gel may become tough in the radial direction and very very weak in the transverse direction. This may be because in rapid extension and cooling of the melt or molten gel, the styrene domains forms clyinderically along the transverse axis in the solid state and is very weak under tension. It may be possible to cure this weakness by annealing the extruded gel at or near the polystyrene melting point. On the other hand, When an optically clear gel is extruded by a rotating cone or plate elastic energy method of extrusion, the extruded gel can also become highly oriented, but in the radial direction which results in a very strong gel when extended in the transverse direction as well as a tough gel in the radial direction. Consequently, oriented fluffy gels can be very weak or strong depending of the methods selected for making articles from such fluffy gels.

Not only do the fluffy gels have all the desirable combination of physical and mechanical properties substantially similar to high viscosity amorphous S-EB-S gels such as high elongation at break of at least 1,600%, ultimate tensile strength of about $8\times10^5$ dyne/cm$^2$ and higher, low elongation set at break of substantially not greater than about 2%, substantially about 100% snap back when extended to 1,200% elongation, and a gel rigidity of substantially from about 2 gram to about 3,000 gram Bloom and higher, the fluffy gels of the present invention exhibit improved tear resistance and resistance to fatigue not obtainable from amorphous S-EB-S or S-EP-S gels at corresponding gel rigidities.

The fluffy gels of the present invention exhibit one or more of the following properties. These are: (1) tensile strength of about from less than about $8\times10^5$ dyne/cm$^2$ to about $10^7$ dyne/cm$^2$ and greater; (2) elongation of less than about 200% to about 3,000% and higher; (3) elasticity modules of less than about $10^4$ dyne/cm$^2$ to about $10^6$ dyne/cm$^2$ and greater; (4) shear modules of less than about $10^4$ dyne/cm$^2$ to about $10^6$ dyne/cm$^2$ and greater as measured with a 1, 2, and 3 kilogram load at 23° C.; (5) gel rigidity of about less than about 2 gram Bloom to about 3,000 gram Bloom and higher as measured by the gram weight required to depress a gel a distance of 4 mm with a piston having a cross-sectional area of 1 square cm at 23° C.; (6) tear propagation resistance from less than about 1.5 kg/cm to about 5.6 kg/cm or higher (the tear resistance of fluffy crystal gels being advantageously greater than that of fluffy amorphous gels); (7) resistance of the fluffy crystal gels to fatigue being advantageously greater than the fatigue resistance of fluffy amorphous gels at corresponding gel rigidities; (8) and substantially 100% snap back recovery when extended at a crosshead separation speed of 25 cm/minute to 200% at 23° C. Properties (1), (2), (3), and (6) above are measured at a crosshead separation speed of 25 cm/minute at 23° C.

The molded fluffy crystal (-E- midblock segment) gel articles have additional important advantages in that the end-use performance properties are advantageously greater than amorphous -EB- and -EP- midblock segment block copolymer gels in that they are more resistant to cracking, tearing, crazing or rupture in flexural, tension, compression, or other deforming conditions of use. Like amorphous gels, the molded articles made from the instant composition possess the intrinsic properties of elastic memory enabling the articles to recover and retain its original molded shape after many extreme deformation cycles.

Not only is the fluffy gels of the invention advantageous for use in making toys, the novel fluffy crystal gels because of their improved properties find other piratical uses. Because of their improved tear resistance and improved resistance to fatigue, the fluffy crystal gels of the present invention achieve greater performance than amorphous gels in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components.

Because of their improved tear resistance and improved resistance to fatigue, the fluffy crystal gels are more useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, as tips for swabs, as fishing bate, as a high vacuum seal (against atmosphere pressure) which contains a useful amount of a mineral oil-based magnetic fluid particles, etc. Moreover, the casted, extruded, or spun threads, strips, yarns, tapes can be weaved into cloths, fine or coarse fabrics.

The fluffy gels can be formed in any shape; the original shape can be deformed into another shape (to contact a regular or irregular surface) by pressure and upon removal of the applied pressure, the composition in the deformed shape will recover back to its original shape.

As an example of the versatility of use of the instant fluffy crystal gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, other foams, or any other desired material or combinations thereof. Moreover, the composition can be casted onto such materials, provided such materials substantially maintain their integrity (shape, appearance, texture, etc.) during the casting process. The same applies for brace cushions, liners, linings and protective coverings for the hand, wrist, finger, forearm, knee, leg, and the like having highly reduce weight. The fluffy gels are advantageously useful as cushions, liners, and coverings which interfaces the body or parts of the body with artificial devices.

Because of their improved tear resistance and resistance to fatigue, the fluffy crystal gels exhibit versatility as materials formed into hollowed thick wall body shapes for use in deep sea ice water diving or insulating the body from extreme cold. Since the fluffy crystal gels are more tear resistant, they are especially useful for making toys and balloons, and insulating gloves. As toy balloons, the fluffy crystal gels are safer because it will not rupture or explode when punctured as would latex balloons which often times cause injures or death to children by choking from pieces of latex rubber. The fluffy crystal gels are advantageously useful for making one layer gloves for vibration damping which prevents damage to blood capillaries in the fingers and hand caused by handling strong shock and vibrating equipment.

Other uses include self sealing enclosures for splicing electrical and telephone cables and wires. For example, the fluffy crystal gels can be pre-formed into a small diameter tubing within an outer elastic tubing, both the internal fluffy crystal gel tubing and external elastic tubing can be axially expanded and fixed in place by a removable continuous retainer. Upon insertion of a spliced pair or bundle of cables or wires, the retainer can be removed, as the retainer is removed, the fluffy crystal gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed.

In all cases, the tear strength of fluffy crystal gels are higher than that of amorphous gels. For example, the fluffy crystal gels made from high viscosity S-E-EB-S and S-E-EP-S copolymers are resistant to tearing when sheared than high viscosity amorphous S-EB-S and S-EP-S copolymer gels. This can be demonstrated by forming a very soft gel samples, for example 100 parts copolymer to 800 parts plasticizing oil. The soft gel is made in a 16 mm×150 mm test tube, the gel cylinder is cut or notched at one point about its cross-section and gripped lengthwise tightly in the left hand about this cross-section point and a length of exposed gel is gripped lengthwise around the adjacent cross-section point tightly by the right hand as close to the left hand as possible without stretching. With the two hands gripping the gel sample's cross-section about the notched point, the hands are moved in opposite directions to tear apart the gel sample at the cross-section point. The shearing action by the gripping hands is done at the fastest speed possible as can be performed by human hands. Using this demonstration, the fluffy crystal gels will not easily break or tear completely apart, whereas, amorphous S-EB-S and S-EP-S gels break or tears apart easily. Likewise the various fluffy crystal gels of the invention described herein are tested and found to be more tear resistant than fluffy amorphous gels. For toys such as airfoils, the improved lower density and resistance to tearing are essential for acceptable performance during play.

The invention is further illustrated by means of the following illustrative embodiments, which are given for purpose of illustration only and are not meant to limit the invention to the particular components and amounts disclosed.

EXAMPLE I

Unexpanded methacrylonitrile microspheres #051, #053, #091, #091-80, and #092-120 as obtained from Expandcel, In., are dispersed in Duraprime 70 white oil in varying amounts to yield oil/microsphere mixtures having the following approximate viscosities (poise): 0.5, 0.8, 1.5, 18, 34, 100, 150, 250, 400, 460, 480, 560, 720, 1000, and 2000.

EXAMPLE II

Gels of 100 parts of high viscosity linear amorphous S-EB-S (Kraton G1651) block copolymer and 1,600, 1,200, 1,000, 800, 600, 500, 450, 300, 250 parts by weight of Duraprime 70 white oil (plasticizer) are melt blended in an anchor mixer to obtain clear molten gels at selected temperatures and viscosities which are dependent on the parts by weight of oil and resultant molten viscosity (as denoted by: parts oil/temperature ° F./poise) as follows: 1,600 @275° F./15–30 poise, 1,200 @280° F./18–25 poise, 1,000 @300° F./20–35 poise, 800 @310° F./30–60 poise, 600 @325° F./50–120 poise, 500 @350° F./100–300 poise, 450 @375° F./150–400 poise, 300 @400° F./200–400 poise, and 250 @425° F./300–500 poise.

EXAMPLE III

Gels of 100 parts of high viscosity linear Kuraray SEPTON 2006 (amorphous S-EP-S) block copolymer and 1,600, 1,200, 1,000, 800, 600, 500, 450, 300, 250 parts by weight of Duraprime 70 white oil (plasticizer) are melt blended in an anchor mixer to obtain clear molten gels at selected temperatures and viscosities which are dependent on the parts by weight of oil and resultant molten viscosity (as denoted by: parts oil/temperature ° F./poise) as follows: 1,600 @275° F./15–30 poise, 1,200 @280° F./18–25 poise, 1,000 @300° F./20–35 poise, 800 @310° F./30–60 poise, 600 @325° F./50–120 poise, 500 @350° F./100–300 poise, 450 @375° F./150–400 poise, 300 @400° F./200–400 poise, and 250 @425° F./300–500 poise.

Note: As the viscosity of the oil used is increase (from Duraprime 70 to 200, 300, 350, 400, etc.) so will the resultant viscosities of the oil/unexpanded thermoplastic particular mixtures and the molten gel viscosities change. As the oil viscosity is increased, the tack of the fluffy gels will increase substantially. The quantity and viscosity of the particulate mixtures of Examples I selected for dispersion in the molten gels of Examples II and III depends on the final fluffy gel density desired and the molten gel viscosity and temperature as well as the approximate amount of time necessary for adequate dispersion of the particulate mixture in the molten gel.

EXAMPLE IV

Step 1: Determine the amounts of unexpanded particulate/oil mixture needed to yield the desired fluffy gel densities and match the viscosity of the mixtures of Examples I with the viscosities of the molten gels of Examples II and III. Step 2: add additional amounts of component II as necessary to the matched Example I mixture selected to obtain the particulate dispersion time (mixing time) required based on the temperatures and viscosities of the molten gels of Examples II and III {i.e., $\frac{1}{10}(t_u)$, $\frac{1}{5}(t_u)$, $\frac{1}{3}(t_u)$, $\frac{1}{4}(t_u)$, $\frac{1}{2}(t_u)$, and $(t_u)$, etc.,}. Step 3: while continuing heating and mixing the molten gels of Examples II and III, add the selected amounts of unexpanded particulate/oil mixtures. Step 4: pressed, molded and extruded into various forms and shapes the resulting fluffy gels at mixing temperatures above 250° F. Step 5: allow part of the fluffy gels to cool to room temperature and then formed it into articles by reheating the fluffy gels above 300° F. under pressure. The fluffy gels and articles made by this procedure are found to exhibit adequate uniform dispersion of the expanded microspheres for densities of about 0.7 g/cm$^3$, 0.65 g/cm$^3$, 0.60 g/cm$^3$, 0.55 g/cm$^3$, 0.50 g/cm$^3$, 0.45 g/cm$^3$, 0.40 g/cm$^3$, 0.35 g/cm$^3$, 0.30 g/cm$^3$, and 0.28 g/cm$^3$. The fluffy gels are found to exhibit gel rigidities of from about 20 to about 3,000 gram Bloom, and elongations of at least 200%.

EXAMPLE V

Procedures of Example IV is repeated using high viscosity crystalline midblock segment linear S-E-EB-S and (S-E-EB)$_n$ multi-arm block copolymers (n=2, 3, 4, and 5) with ethylene to ethylene/butylene midblock ratios (E:EB) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30. It is found the procedure of the Example is capable of producing fluffy gels of about 0.6 g/cm$^3$ to about 0.30 g/cm$^3$, gel rigidities of from about 20 to about 3,000 gram Bloom, elongations of at least 200%, and the tensile strength, notched tear strength, and resistance to fatigue are found to be greater than that of fluffy amorphous gels of Examples IV.

EXAMPLE VI

Procedures of Example IV is repeated using high viscosity crystalline midblock segment linear S-E-EP-S and radial (S-E-EP)$_n$ multi-arm block copolymers. It is found the procedure of the Example is capable of producing fluffy gels of about 0.6 g/cm$^3$ to about 0.30 g/cm$^3$, gel rigidities of from about 20 to about 3,000 gram Bloom, elongations of at least 200%, and the tensile strength, notched tear strength, and resistance to fatigue are found to be greater than that of fluffy amorphous gels of Examples IV.

EXAMPLE VII

Procedures of Example IV is repeated using high viscosity crystalline midblock segment linear (S-B-S), (S-B-EP-S), (S-B-EB-S),(S-B-EP-B-S), (S-B-EB-B-S), (S-B-EB-EP-S), (S-B-EP-EB-S), (S-EB-EP-S), (S-EP-B-EP-S), (S-B-EB-B-EB-S), (S-B-EB-B-EP-S) and (S-B-EP-B-EP-B-S) block copolymers. It is found the procedure of the Example is capable of producing fluffy gels of about 0.6 g/cm$^3$ to about 0.30 g/cm$^3$, gel rigidities of from about 20 to about 3,000 gram Bloom, elongations of at least 200%, and the tensile strength, notched tear strength, and resistance to fatigue are found to be lower than that of fluffy crystal gels of Examples V and VI.

EXAMPLE VIII

Example IV is repeated using high viscosity crystalline midblock segment linear (S-E-EB$_{25}$-S), (S-EP-E-EP-S), (S-E-EB-S), (S-E-EP-S), (S-E-EP-E-S), (S-E-EB-B-S), (S-E-B-EB-S), (S-E-B-EP-S), (S-E-EB-EP-S), (S-E-EP-EB-S), (S-E-EP-E-EP-S), (S-E-EP-E-EB-S), (S-E-EB-B-EP-S), (S-E-EP-B-EB-S), (S-E-EP-E-EP-E-S), (S-E-EP-E-EB-S), (S-E-EP-E-EP-EB-S), (S-E-EP-E-EP-E-S), and (S-E-EP-EB-EP-EB-B-S) block copolymers. It is found the procedure of the Example is capable of producing fluffy gels of about 0.6 g/cm³ to about 0.30 g/cm³, gel rigidities of from about 20 to about 3,000 gram Bloom, elongations of at least 200%, and the tensile strength, notched tear strength, and resistance to fatigue are found to be greater than that of amorphous gels of Example IV.

EXAMPLE IX

Example IV is repeated using high viscosity polyurethane elastomers formed from a hydroxyl terminated poly (ethylene-butylene) oligomer having TMP/diisocyanate and BEPD/diisocyanate copolymer crystalline groups. The fluffy polyurethane elastomer gels are formed at between about 375° C. to about 450° C. It is found the procedure of the Example is capable of producing fluffy gels of about 0.6 g/cm³ to about 0.30 g/cm³, gel rigidities of from about 20 to about 3,000 gram Bloom, elongations of at least 200%, and the tensile strength, notched tear strength, and resistance to fatigue are found to be greater than that of amorphous gels of Example IV.

EXAMPLE X

Example IV is repeated using high viscosity crystalline midblock segment multiarm $(S-E-EB)_n$, $(S-E-EP)_n$, $(S-E-EP-E)_n$, $(S-E-EB-B)_n$, $S-E-B-EB)_n$, $(S-E-B-EP)_n$, $(S-E-EB-EP)_n$, $(S-E-EP-EB)_n$, $(S-E-EP-E-EP)_n$, $(S-E-EP-E-EB)_n$, $(S-E-EB-B-EP)_n$, $(S-E-EP-B-EB)_n$, $(S-E-EP-E-EP-E)_n$, $(S-E-EP-E-EB)n$, $(S-E-EP-E-EP-EB)n$, $(S-E-EP-E-EP-E)n$, and $(S-E-EP-EB-EP-EB-B)n$, with n=2, 3, 4, and 5 block copolymers. It is found the procedure of the Example is capable of producing fluffy gels of about 0.6 g/cm³ to about 0.30 g/cm³, gel rigidities of from about 20 to about 3,000 gram Bloom, elongations of at least 200%, and the tensile strength, notched tear strength, and resistance to fatigue are found to be greater than that of amorphous gels of Example IV.

EXAMPLE XI

Examples IV, V, VI, VII and VIII are repeated with the addition of 2, 5, and 10 parts by weight of ethylene-butyl acrylate, ethylene-ethyl acrylate, ethylene-methyl acrylate, ethylene-vinyl acetate, acrylonitrile-styrene-acrylate, styrene-acrylonitrile, styrene-maleic anhydride, meleated poly(styrene-ethylene-propylene-styrene) and meleated poly(styrene-ethylene-butylene-styrene). It is found the procedure of the Examples is capable of producing fluffy gels of about 0.6 g/cm³ to about 0.30 g/cm³, gel rigidities of from about 20 to about 3,000 gram Bloom, elongations of at least 200% and when the fluffy gels are formed with various substrates, such as fabric, the shedding of expanded microspheres at the fluffy gel and fabric interface at the tests areas of fatigue failure appears to be reduced.

EXAMPLE XII

Example IX is repeated using high viscosity polyurethane elastomers formed from hydroxyl terminated poly(ethylene-propylene), poly(ethylene-ethylene/butylene), poly(ethylene-ethylene/propylene), and poly(butylene) oligomers having TMP/diisocyanate and BEPD/diisocyanate copolymer crystalline groups. The fluffy polyurethane elastomer gels are formed at between about 375° C. to about 450° C. It is found the procedure of the Example is capable of producing fluffy gels of about 0.6 g/cm³ to about 0.30 g/cm³, gel rigidities of from about 20 to about 3,000 gram Bloom, elongations of at least 200%, and the tensile strength, notched tear strength, and resistance to fatigue are found to be greater than that of fluffy amorphous gels of Example IV.

EXAMPLE XIII

Examples IV, V, VI, VII and VIII are repeated with the addition of 2, 5, and 10 parts by weight of Dowlex 3010, 2077, Dow Affinity ethylene alpha-olefin resin PL-1840, SE-1400, SM-1300, Dow Elite 5100, 5200, 5400, Dow Attane (ultra low density ethylene-octene-1 copolymers) 4803, and 4602. It is found the procedure of the Examples is capable of producing fluffy gels of about 0.6 g/cm³ to about 0.30 g/cm³, gel rigidities of from about 20 to about 3,000 gram Bloom, elongations of at least 200% and the tear and rupture resistance of the fluffy gels containing the polyolefins appear to improve over the fluffy gels absent such polyolefins.

While preferred components and formulation ranges have been disclosed herein persons of skill in the art can extend these ranges using appropriate material according to the principles discussed herein. Furthermore, Crystalline midblock segment block polymers can be use in blending with other engineering plastics and elastomeric polymers to make alloyed compositions having improved impact and tear resistance properties. All such variations and deviations which rely on the teachings through which the present invention has advanced the art are considered to be within the spirit and scope of the present invention and it is not intended to limit the invention to the exact details shown above except insofar as they are defined in the following claims.

What I claim is:

1. A gel comprising a fluffy, solid, strong elastic gelatinous elastomer composition, $G_n$, exhibiting resistance to elastic deformation, capable of shape-memory recovery, being dimensionally stable formed from (I) 100 parts by weight of at least one or more a linear, multi-arm, branched, or star shaped high viscosity block copolymer, (II) about 300 to about 1,600 parts by weight of a plasticizing oil, (III) a selected amount of one or more heat expandable plastic or synthetic particulates of material dispersed in one or more predetermined ordered or separate phases, said dispersed particulate material being capable of producing a predetermined selected volume of closed cell particulate dispersion forming said gel, wherein said gel having a density of at least about 0.70 g/cm³, a gel rigidity of from about 20 to about 3,000 gram Bloom, and an elongation of at least 200%, said gel capable of being formed with or physically interlocked with a selected substrate material, $M_n$, to form one or more combinations of a gel-substrate composites including a sequential addition or permutation of said combinations of one or more gels of the same or different gel rigidity and one or more substrates of the same or different material; said gel formed with or without (IV) one or more of a selected polar polymer and in combination with or without (V) one or more of a selected crystalline or non-crystalline polymer or copolymer.

2. A gel according to claim 2 having a density of about 0.70 g/cm³, 0.65 g/cm³, 0.60 g/cm³, 0.55 g/cm³, 0.50 g/cm³, 0.45 g/cm³, 0.40 g/cm³, 0.35 g/cm³, 0.30 g/cm³, or 0.28 g/cm³.

3. A gel according to claim 2, wherein said $G_n$ as denoted by the subscript n is the same or different gel or gel rigidity and $M_n$, as denoted by the subscript n is the same or different substrate selected from the group consisting of foam, plastic, fabric, metal, concrete, wood, glass, ceramics, synthetic resin, synthetic fibers or refractory materials.

4. A gel according to claim 3, wherein said $G_n$ is formed with or physically interlocked with said material $M_n$ to form a composite of the combination $M_n G_n$, $G_n M_n G_n$, $M_n G_n M_n$, $M_n G_n G_n$, $M_n M_n G_n$, $M_n G_n G_n G_n$, $M_n M_n M_n G_n$ or one or more of the same or different sequential additions or one or more of the same or different permutations of said combination.

5. A gel according to claim 2, wherein said (I) block copolymer is poly(styrene-ethylene-butylene-styrene), poly(styrene-ethylene-propylene-styrene), poly(styrene-ethylene-styrene), poly(styrene-butylene-styrene), poly(styrene-ethylene-ethylene/butylene-styrene), poly(styrene-ethylene-ethylene/propylene-styrene), poly(styrene-butylene-ethylene/propylene-styrene), poly(styrene-butylene-ethylene/butylene-styrene), poly(styrene-ethylene-ethylene/propylene-ethylene-styrene), poly(styrene-ethylene-ethylene/butylene-butylene-styrene), poly(styrene-butylene-ethylene/propylene-butylene-styrene), poly(styrene-butylene-ethylene/butylene-butylene-styrene), poly(styrene-ethylene-butylene-ethylene/butylene-styrene), poly(styrene-ethylene-butylene-ethylene/propylene-styrene), poly(styrene-ethylene-butylene-ethylene/propylene-styrene), poly(styrene-ethylene-ethylene/butylene-ethylene/propylene-styrene), poly(styrene-ethylene-ethylene/butylene-styrene), poly(styrene-butylene-ethylene/butylene-ethylene/propylene-styrene), poly(styrene-butylene-ethylene/propylene-ethylene/butylene-styrene), poly(styrene-ethylene-ethylene/propylene-ethylene-ethylene/propylene-styrene), poly(styrene-ethylene-ethylene/propylene-ethylene-ethylene/butylene-styrene), poly(styrene-ethylene/propylene-butylene-ethylene/propylene-styrene), poly(styrene-butylene-ethylene/butylene-butylene-ethylene/butylene-styrene), poly(styrene-butylene-ethylene/butylene-butylene-ethylene/propylene-styrene), poly(styrene-ethylene-ethylene/butylene-butylene-ethylene/propylene-styrene), poly(styrene-ethylene-ethylene/propylene-butylene-ethylene/butylene-styrene), poly(styrene-ethylene-ethylene/propylene-ethylene/propylene-ethylene-styrene), poly(styrene-butylene-ethylene/propylene-butylene-ethylene/propylene-butylene-styrene), poly(styrene-ethylene-ethylene/propylene-ethylene-ethylene/butylene-styrene), poly(styrene-ethylene-ethylene/propylene-ethylene-ethylene/propylene-butylene-styrene), poly(styrene-ethylene-ethylene/propylene-ethylene-ethylene/propylene-ethylene-styrene), poly(styrene-ethylene-ethylene/propylene-ethylene/butylene-ethylene/propylene-ethylene/butylene-styrene), poly(styrene-ethylene-butylene)$_n$, poly(styrene-ethylene-propylene)$_n$, poly(styrene-ethylene)$_n$, poly(styrene-butylene)$_n$, poly(styrene-ethylene-ethylene/butylene)$_n$, poly(styrene-ethylene-ethylene/propylene)$_n$, poly(styrene-butylene-ethylene/propylene)$_n$, poly(styrene-butylene-ethylene/butylene)$_n$, poly(styrene-ethylene-ethylene/propylene-ethylene)$_n$, poly(styrene-ethylene-ethylene/butylene-butylene)$_n$, poly(styrene-butylene-ethylene/butylene-butylene)$_n$, poly(styrene-ethylene-butylene-ethylene/butylene)$_n$, poly(styrene-ethylene-butylene-ethylene/propylene)$_n$, poly(styrene-ethylene-butylene-ethylene/propylene)$_n$, poly(styrene-ethylene-ethylene/butylene-ethylene/propylene)$_n$, poly(styrene-ethylene-ethylene/propylene-ethylene/butylene)$_n$, poly(styrene-butylene-ethylene/butylene-ethylene/propylene)$_n$, poly(styrene-butylene-ethylene/propylene-ethylene/butylene)$_n$, poly(styrene-ethylene-ethylene/propylene-ethylene-ethylene/propylene)$_n$, poly(styrene-ethylene-ethylene/propylene-ethylene-ethylene/butylene)$_n$, poly(styrene-ethylene/propylene-butylene-ethylene/propylene)$_n$, poly(styrene-butylene-ethylene/butylene-butylene-ethylene/butylene)$_n$, poly(styrene-butylene-ethylene/butylene-butylene-ethylene/propylene)$_n$, poly(styrene-ethylene-ethylene/butylene-butylene-ethylene/propylene)$_n$, poly(styrene-ethylene/butylene-butylene-ethylene/propylene)$_n$, poly(styrene-ethylene-ethylene/propylene-ethylene-ethylene/propylene-ethylene)$_n$, poly(styrene-ethylene-ethylene/propylene-ethylene-ethylene/propylene-ethylene/butylene)$_n$, poly(styrene-ethylene-ethylene/propylene-ethylene/butylene-ethylene/propylene-ethylene/butylene-butylene)$_n$ or a mixture thereof.

6. A gel according to claim 2, wherein said (IV) polar polymer is ethylene-butyl acrylate, ethylene-ethyl acrylate, ethylene-methyl acrylate, ethylene-vinyl acetate, ethylene-vinyl acrylate, ethylene-vinyl alcohol, acrylonitrile-styrene-acrylate, styrene-acrylonitrile, styrene-maleic anhydride, meleated poly(styrene-ethylene-propylene-styrene), meleated poly(styrene-ethylene-butylene-styrene) or a mixture thereof.

7. A gel according to claim 2, wherein said selected (V) crystalline or non-crystalline polymer or copolymer is poly(styrene-butadiene-styrene), poly(styrene-butadiene), poly(styrene-isoprene-styrene), poly(styrene-isoprene), poly(styrene-ethylene-propylene), low viscosity poly(styrene-ethylene-propylene-styrene), low viscosity poly(styrene-ethylene-butylene-styrene), poly(styrene-ethylene-butylene), meleated poly(styrene-ethylene-butylene-styrene), high vinyl content poly(styrene-ethylene-butylene-styrene) poly(styrene-ethylene-propylene-styrene-ethylene-propylene), poly(ethylene-propylene), poly(styrene-butadiene)$_n$, poly(styrene-butadiene)n, poly(styrene-isoprene)$_n$, poly(styrene-isoprene)$_n$, poly(styrene-ethylene-propylene)$_n$, low viscosity poly(styrene-ethylene-propylene)$_n$, low viscosity poly(styrene-ethylene-butylene)$_n$, poly(styrene-ethylene-butylene)$_n$, meleated poly(styrene-ethylene-butylene)$_n$, high vinyl content poly(styrene-ethylene-butylene)$_n$, poly(styrene-ethylene-propylene-styrene-ethylene-propylene)$_n$, poly(ethylene-propylene)$_n$, polystyrene, polybutylene, poly(ethylene-propylene), poly(ethylene-butylene), polypropylene, polyethylene, polypthalamide or polyurethane elastomer formed from one or more saturated hydrocarbon diols, wherein said selected block copolymer is a linear, branched, multiarm, or star shaped copolymer.

8. A gel according to claim 2, wherein said gel is a crystal gel formed from one or more (I) block copolymers having a selected amount of crystallinity sufficient to exhibit a melting endotherm of at least about 40° C. as determined by DSC curve.

9. A gel according to claim 2, wherein said gel exhibits in differential scanning calorimeter (DSC) a melting endotherm of about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

10. A gel according to claim 2, wherein said (I) copolymer of said gel is a thermoplastic polyurethane elastomer made with diisocyanates and chain extenders 2,2,4-trimethyl1,3-pentancdiol or 2-Butyl-2-ethyl-1,3-pentanediol and a saturated hydrocarbon diol, said polyurethane having one or more crystalline groups of about 22% to about 45% wy weight of said elastomer and capable of exhibiting a glass transition of at least about −40° C.

11. A gel according to claim 10, wherein said hydrocarbon diols is a hydroxyl terminated oligomer of poly(ethylene-butylene) or poly(ethylene-propylene).

12. A gel according to claim 2, wherein said gel is capable of exhibiting a full recovery delay time of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 120 seconds after extension or deformation.

13. A gel according to claim 2, wherein said selected amount of particulates of material is a thermoplastic polymer of methacrylonitrile containing a hydrocarbon liquid, said particulates capable of being soften by heat thereby transforming said hydrocarbon liquid into a vapor state and expanding said particulates into a predetermined closed cell volume of expanded microspheres, said closed cell expanded microspheres being substantially dispersed to form said fluffy gelatinous elastomer composition.

* * * * *